United States Patent
Ishimaru et al.

(10) Patent No.: US 9,551,670 B2
(45) Date of Patent: Jan. 24, 2017

(54) SURFACE INSPECTION APPARATUS AND METHOD THEREOF

(71) Applicant: Hitachi High-Technologies Corporation, Tokyo (JP)

(72) Inventors: Ichiro Ishimaru, Mure (JP); Minori Noguchi, Mitsukaidou (JP); Ichiro Moriyama, Hamura (JP); Yoshikazu Tanabe, Irima (JP); Yasuo Yatsugake, Kamisato (JP); Yukio Kenbou, Tokyo (JP); Kenji Watanabe, Oume (JP); Hirofumi Tsuchiyama, Hitachinaka (JP)

(73) Assignees: HITACHI, LTD., Tokyo (JP); HITACHI HIGH-TECHNOLOGIES CORPORATION, Tokyo (JP)

( * ) Notice: Subject to any disclaimer, the term of this patent is extended or adjusted under 35 U.S.C. 154(b) by 310 days.

(21) Appl. No.: 14/249,512

(22) Filed: Apr. 10, 2014

(65) Prior Publication Data
US 2014/0218723 A1    Aug. 7, 2014

Related U.S. Application Data

(63) Continuation of application No. 13/114,160, filed on May 24, 2011, now Pat. No. 8,729,514, which is a
(Continued)

(30) Foreign Application Priority Data

Mar. 8, 2000 (JP) .................................. 2000-068593

(51) Int. Cl.
*G01N 21/88* (2006.01)
*G01N 21/47* (2006.01)
(Continued)

(52) U.S. Cl.
CPC ............ *G01N 21/88* (2013.01); *G01N 21/474* (2013.01); *G01N 21/94* (2013.01);
(Continued)

(58) Field of Classification Search
CPC .. G01N 21/9501; G01N 21/94; G01N 21/956; G01N 2021/8822; G01N 21/47; G01N 21/8806; G01N 21/8851; G01N 21/9505; G01N 2021/8861
See application file for complete search history.

(56) References Cited

U.S. PATENT DOCUMENTS

| 4,449,818 A | 5/1984 | Yamaguchi et al. |
| 4,889,998 A | 12/1989 | Hayano et al. |

(Continued)

FOREIGN PATENT DOCUMENTS

| JP | 54-128682 | 10/1979 |
| JP | 56-086340 | 7/1981 |

(Continued)

*Primary Examiner* — Hoon Song
(74) *Attorney, Agent, or Firm* — Baker Botts L.L.P.

(57) ABSTRACT

A defect inspection apparatus including: a first illumination optical system which is configured to illuminate the inspection area on a sample surface from a normal line direction or a direction near thereof with respect to said sample surface; a second illumination optical system which is configured to illuminate said inspection area from a slant direction with respect to said sample surface; a detection optical system having a plurality of first detectors which are located, in front of, on the sides of, and behind said inspection area, respectively, with respect to the illumination direction of said second illumination optical system, and where the regular reflected light component, from said sample surface, by illumination light of said second illumination optical system, is not converged; and a signal processing system
(Continued)

which is configured to inspect a defect, upon basis of signals obtained from said plurality of first detectors.

11 Claims, 33 Drawing Sheets

Related U.S. Application Data continuation of application No. 12/196,647, filed on Aug. 22, 2008, now Pat. No. 7,952,085, which is a continuation of application No. 11/657,455, filed on Jan. 25, 2007, now Pat. No. 7,417,244, which is a continuation of application No. 11/104,621, filed on Apr. 13, 2005, now Pat. No. 7,242,016, which is a continuation of application No. 09/791,742, filed on Feb. 26, 2001, now Pat. No. 6,894,302.

(51) Int. Cl.
   *G01N 21/94* (2006.01)
   *G01N 21/95* (2006.01)

(52) U.S. Cl.
   CPC ..... *G01N 21/9501* (2013.01); *G01N 21/9503* (2013.01); *G01N 2021/8825* (2013.01); *G01N 2021/8854* (2013.01)

(56) References Cited

U.S. PATENT DOCUMENTS

| | | | |
|---|---|---|---|
| 5,486,919 A | 1/1996 | Tsuji et al. | |
| 5,712,701 A | 1/1998 | Clementi et al. | |
| 5,903,342 A * | 5/1999 | Yatsugake | G01N 21/94 250/559.41 |
| 6,081,325 A | 6/2000 | Leslie et al. | |
| 6,104,481 A | 8/2000 | Sekine et al. | |
| 6,256,093 B1 * | 7/2001 | Ravid | G01N 21/9501 356/237.2 |
| 6,366,352 B1 | 4/2002 | Goldberg et al. | |
| 6,469,784 B2 | 10/2002 | Golberg et al. | |
| 6,894,302 B2 | 5/2005 | Ishimaru et al. | |
| 2002/0036771 A1 | 3/2002 | Sato et al. | |
| 2002/0041374 A1 | 4/2002 | Ohshima et al. | |

FOREIGN PATENT DOCUMENTS

| | | |
|---|---|---|
| JP | 57-013340 | 1/1982 |
| JP | 57-132044 | 8/1982 |
| JP | 63-033649 | 2/1988 |
| JP | 2-028815 | 6/1990 |
| JP | 03-102248 | 4/1991 |
| JP | 03-102249 | 4/1991 |
| JP | 03-108735 | 5/1991 |
| JP | 04-061142 | 2/1992 |
| JP | 05-340883 | 12/1993 |
| JP | 06-003123 | 1/1994 |
| JP | 09-304289 | 11/1997 |
| JP | 11-064234 | 3/1999 |
| JP | 11-142127 | 5/1999 |
| JP | 11-160245 | 6/1999 |
| JP | 11-284038 | 10/1999 |
| WO | WO 97/35161 | 9/1997 |
| WO | WO 99/67626 | 12/1999 |

* cited by examiner

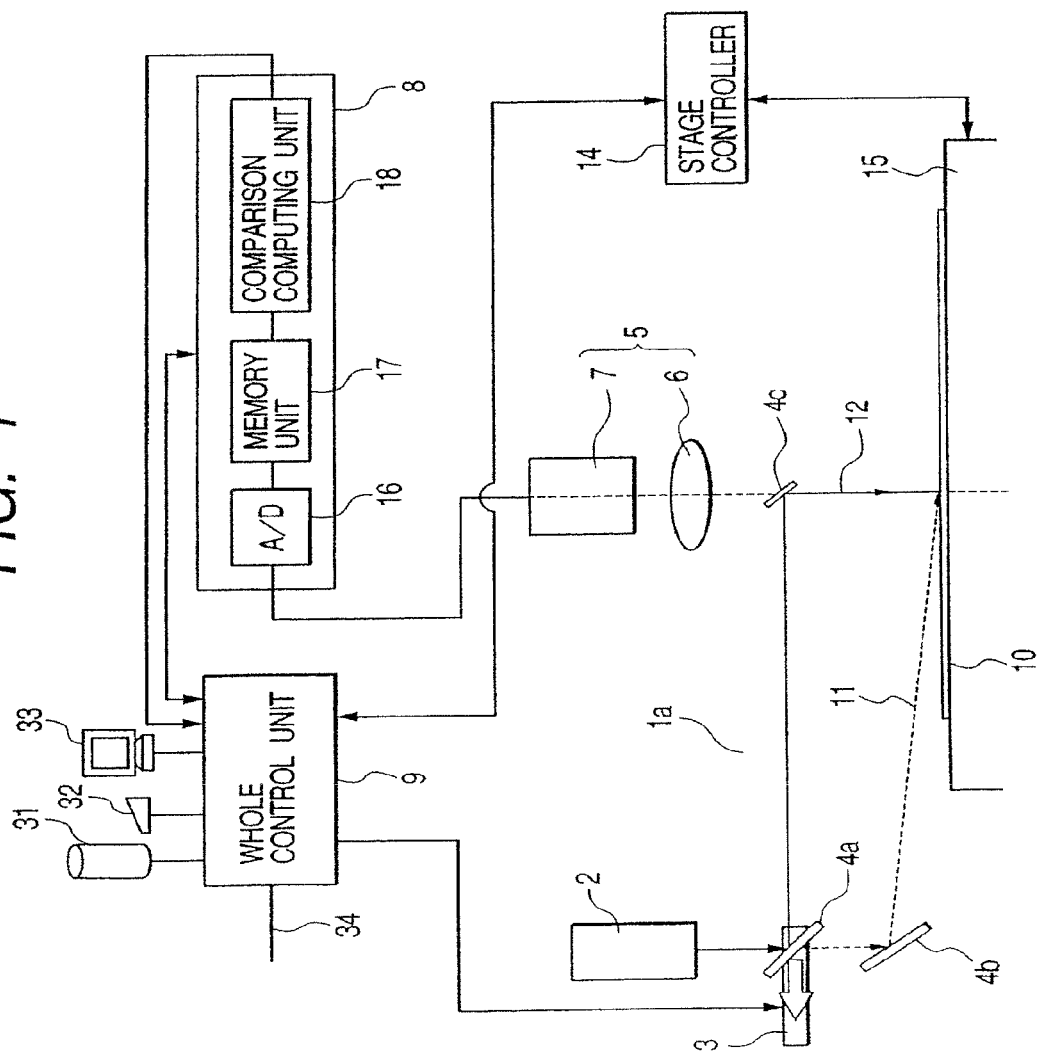

PERPENDICULAR
ILLUMINATION

PSEUDO
PERPENDICULAR
ILLUMINATION

PERPENDICULAR
ILLUMINATION

PERPENDICULAR
ILLUMINATION

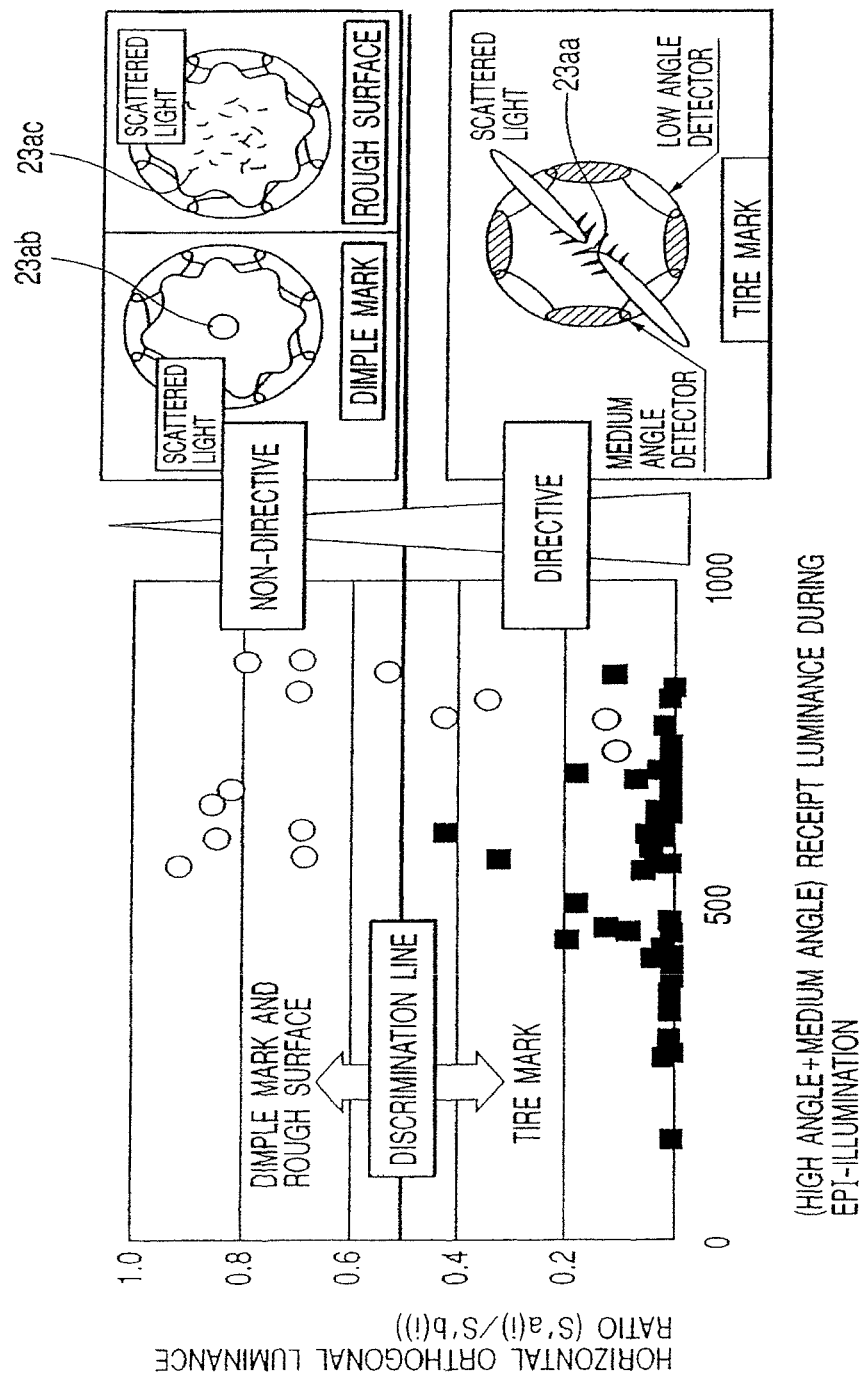

23b

B

A

SEARCH MAXIMUM RECEIPT LUMINANCE CIRCLE A — S65

REFER TO RECEIPT LUMINANCE B IN ORTHOGONAL CIRCLE — S66

CALCULATE LUMINANCE RATIO $(Sa(i)/Sb(i))$ — S67

FIG. 29A
FIG. 29B
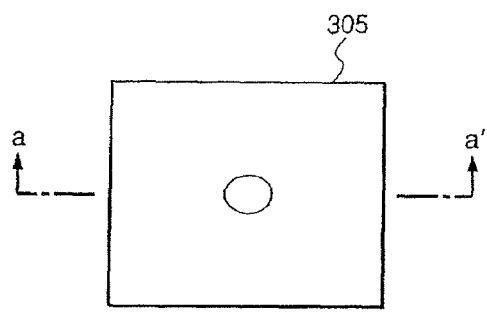
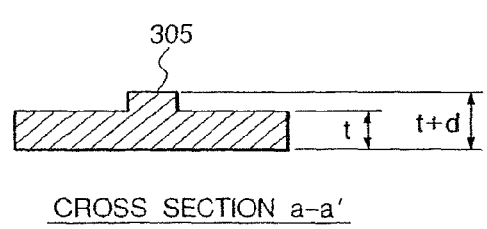
FIG. 30
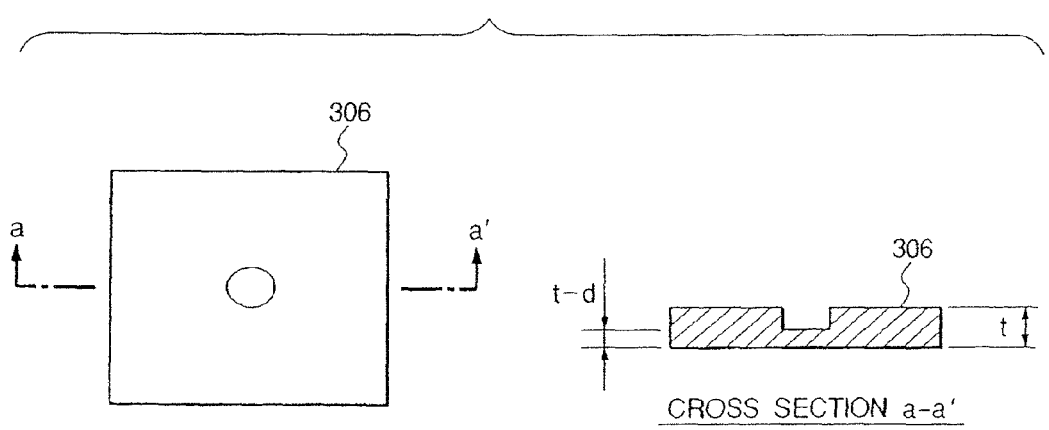

| TARGET | CONVEX (FOREIGN OBJECT 24) | |
|---|---|---|
| SCHEMATIC DIAGRAM | REFERENCE REFLECTED LIGHT / SCATTERED LIGHT (ADVANCE PHASE) 22 / 24 | |
| | PHOTOMULTIPLIER A310 DETECTION INTENSITY | PHOTOMULTIPLIER B307 DETECTION INTENSITY |
| PHASE VECTOR OF EACH PHOTOMULTIPLIER | PHOTOMULTIPLIER A DETECTION LIGHT / 310b / 241 / SCATTERED LIGHT / REFERENCE REFLECTED LIGHT / ADVANCE PHASE REFERENCE REFLECTED LIGHT / 321 | PHOTOMULTIPLIER B DETECTION LIGHT / REFERENCE REFLECTED LIGHT / 307b / 241 / SCATTERED LIGHT / BEHIND PHASE REFERENCE REFLECTED LIGHT / 325 |
| DIFFERENTIAL SIGNAL INTENSITY | DIFFERENTIAL SIGNAL (PHOTOMULTIPLIER A−PHOTOMULTIPLIER B)=POSITIVE | |

FIG. 34

| ITEM | CONCAVE (SCRATCH 23) | | CONVEX (FOREIGN OBJECT 24) | |
|---|---|---|---|---|
| CROSS SECTIONAL CONFIGURATION | 23 / 22 | | 24 / 22 | |
| | IMAGE | LUMINANCE DISTRIBUTION | IMAGE | LUMINANCE DISTRIBUTION |
| ADVANCE PHASE FILTER 306 TRANSMISSION | a — a' | LUMINANCE | b — b' | LUMINANCE |
| ADVANCE PHASE FILTER 305 TRANSMISSION | a — a' | LUMINANCE | b — b' | LUMINANCE |
| DIFFERENTIAL SIGNAL | NEGATIVE | | POSITIVE | |

SURFACE INSPECTION APPARATUS AND METHOD THEREOF

CROSS REFERENCE TO RELATED APPLICATION

This is a continuation of U.S. application Ser. No. 13/114,160, filed May 24, 2011 which is a continuation of U.S. application Ser. No. 12/196,647, filed Aug. 22, 2008 (now U.S. Pat. No. 7,952,085), which is a continuation of U.S. application Ser. No. 11/657,455, filed Jan. 25, 2007 (now U.S. Pat. No. 7,417,244), which is a continuation of U.S. application Ser. No. 11/104,621, filed Apr. 13, 2005 (now U.S. Pat. No. 7,242,016), which is a continuation of U.S. application Ser. No. 09/791,742, filed Feb. 26, 2001 (now U.S. Pat. No. 6,894,302). This application relates to and claims priority from Japanese Patent Application No. 00-068593, filed on Mar. 8, 2000. The entirety of the contents and subject matter of all of the above is incorporated herein by reference.

BACKGROUND OF THE INVENTION

The present invention relates to a surface inspection apparatus and a method thereof for discriminatingly inspecting defects such as scratches and foreign objects that arise in the flattening process in which polishing or grinding working technique is applied in semiconductor manufacturing processes or magnetic head manufacturing processes.

As for the prior art for discriminatingly inspecting a foreign object that adheres on a semiconductor wafer on which a circuit pattern has been formed from the circuit pattern, Japanese Unexamined Patent Publication No. H3-102248 (prior art 1) and Japanese Unexamined Patent Publication No. H3-102249 (prior art 2) have been known. In detail, a method is described in the prior art 1 and the prior art 2 in which a foreign object on a semiconductor substrate is detected by means of a first photoelectric conversion element with emphasis by use of a slant illumination, and an edge of a circuit pattern that is the background on the semiconductor is detected by means of a second photoelectric conversion element with emphasis by use of an epi-illumination, the foreign detection signal obtained from the above-mentioned first photoelectric conversion element is divided by the detection signal obtained from the second photoelectric element to thereby emphasize the foreign object detection signal, and thus the foreign object is detected.

As for the prior art for discriminatingly inspecting adherent foreign objects on the silicon wafer surface from the crystalline defect on the surface, Japanese Unexamined Patent Publication No. H9-304289 (prior art 3) has been known. In detail, a discriminating inspection method is described in the prior art 3, in which an inspection apparatus is provided with a low angle light receiving system that makes an elevation angle of equal to or smaller than 30 degrees with respect to the surface of the silicon wafer and a high angle light receiving system that makes an elevation angle of larger than that of the low angle light receiving system, the scattered light obtained by irradiating a laser light onto the surface of the silicon wafer approximately perpendicularly is received by the low angle light receiving system and the high angle light receiving system, wherein the light received only by the high angle light receiving system is attributed to the crystalline defect, and the light that is received by both the low angle light receiving system and the high angle light receiving system is attributed to the adherent foreign object.

As for the prior art for discriminatingly inspecting the foreign object or flaw on the surface of a semiconductor wafer from a small dot dimple that is too small to cause the problem in forming of a circuit pattern without mis-discrimination, Japanese Unexamined Patent Publication No. H11-142127 has been known (prior art 4). In detail, an inspection method is described in the prior art 4, in which a low incident angle light and a high incident angle light having wavelengths that are different each other are irradiated in focus on the same point on the surface of a semiconductor wafer with a low incident angle and a high incident angle respectively, the scattered light of two wavelengths from the focused point is received separately and photoelectrically converted, and thus the foreign object and the flaw is discriminated from the dot dimple on the surface of the semiconductor wafer, wherein the intensity difference between signals is utilized, that is, the principle that the intensity of the light irradiated with a low incident angle and scattered from the dot dimple is weak is utilized.

Aside from the above, CMP (Chemical Mechanical Polishing) has been known as a typical (flattening) work technique applied on a work target (for example, insulating film) in the semiconductor manufacturing process or magnetic head manufacturing process. CMP is a (flattening) technique in which free abrasive grains consisting of a material such as silica is spread on a polishing pad and the surface of the work target is polished. Another grinding work technique has been known, in which a work target is polished with use of a pad on which grinding grains consisting of a material such as diamond are embedded fixedly. In such polishing or grinding process, scratches having various configuration, that are polishing flaw or grinding flaw, can be formed on the surface of a work target (for example, an insulating film on a semiconductor substrate (wafer)). If scratches having various configuration are formed on the surface of a work target in the semiconductor manufacturing process or the magnetic head manufacturing process as described hereinabove, a scratch causes insufficient etching in wiring forming and causes the defect such as short-circuit. To eliminate such defect, it is necessary that the polished wafer surface or ground surface is observed after polishing or grinding to monitor the occurrence of scratches having various configuration, and polishing condition or grinding condition must be reviewed correspondingly to the configuration of scratches if the scratch occurs frequently. Furthermore, the foreign object also causes the defect such as defective insulation and short-circuit of wiring to be formed thereon.

If the foreign object occurs frequently, a countermeasure such as cleaning of an equipment is required, and at that time the countermeasure is different from that for scratching. In other words, it is required to monitor discriminatingly between the foreign object and scratch having various configuration, and to apply a countermeasure relevant to the foreign object or scratch in polishing process or grinding process applied on a work target (for example, an insulating film on a semiconductor substrate).

However, any of the prior arts 1 to 4 does not involve inspection for discriminating between the scratch having various configuration and adherent foreign object on the surface of a work target in polishing process or grinding process applied on the work target (for example, an insulating film on a semiconductor substrate).

Generally, because the width W of the scratch having various configuration ranges as small as from 0.2 µm to 0.4 µm, and the depth D ranges as very shallow as from several nm to the deepest 100 nm, a worker visually discriminates between the scratch having various configuration and the foreign object by use of an electron microscope conventionally, but such visual observation requires much time. As the result, the countermeasure for scratch or foreign object is devised delayingly, and many wafers are polished under bad condition to result in much loss of profit.

SUMMARY OF THE INVENTION

The invention provides a surface inspection apparatus and a method for inspecting the surface of a sample that are capable of inspecting discriminatingly between the scratch of various configuration and the adhered foreign object that occur on the surface of a work target when the work target (for example, an insulating film on a semiconductor substrate) is subjected to polishing process such as CMP or grinding process in semiconductor manufacturing process or magnetic head manufacturing process.

Furthermore, the present invention provides a semiconductor substrate manufacturing process in which the defect is inspected discriminatingly between the scratch of various configuration and the adhered foreign object that occur on the surface of a work target when the work target (for example, an insulating film on a semiconductor substrate) is subjected to polishing process such as CMP or grinding process in semiconductor manufacturing process or magnetic head manufacturing process with the total inspection or sufficiently frequent sampling inspection, and as the result the semiconductor substrate having no defect is efficiently manufactured with high reliability.

Furthermore, the present invention provides a surface inspection apparatus and a surface inspection method for inspecting the defect located near the wafer edge of the work target.

In detail, in the present invention, the surface inspection apparatus is provided with a stage on which an inspection target is placed, an illumination optical system having an epi-illumination system for epi-illuminating the inspection target placed on the stage and a slant illumination system for slant-illuminating the surface of the inspection target placed on the stage, a detection optical system having a first converging optical system for converging the first scattered light that comes in the direction of the first desired angle with respect to the surface of the inspection target out of the first reflected light emitted from the inspection target epi-illuminated by means of the epi-illumination system of the illumination optical system and the second scattered light that comes in the direction of the first desired angle out of the second reflected light emitted from the inspection target slant-illuminated by means of the slant illumination system of the illumination optical system and having a first photoelectric conversion means for receiving the first and second scattered lights converged by means of the first converging optical system to thereby convert the received lights to the first and second luminance signals, a comparison discrimination unit for discriminating the defect on the inspection target based on the relation between the first luminance signal and the second luminance signal that have been converted by means of the photoelectric conversion means of the detection optical system, and an output unit for supplying the result obtained by means of the comparison discrimination unit.

Furthermore, in the present invention, the surface inspection apparatus is provided with a stage that is movable in at least two-dimensional direction on which an inspection target is placed, an illumination optical system having an epi-illumination system used for epi-illuminating the inspection target placed on the stage and having a slant illumination optical system used for slant-illuminating the surface of the inspection target, a reflected light detection system having a first reflected light detection unit for detecting the reflected light reflected from the inspection target that is epi-illuminated by means of the epi-illumination system of the illumination optical system and having a second reflected light detection unit for detecting the reflected light reflected from the inspection target that is slant-illuminated by means of the slant illumination system of the illumination optical system, a defect detection system for detecting the defect on the inspection target by use of the output signals of the first reflected light detection unit and the second reflected light detection unit of the reflected light detection system, a defect classification system for classifying the type of the defect detected by means of the defect detection system, and an output unit for generating the defect type information that has been classified by means of the defect classification system.

Furthermore, in the present invention, a method for inspecting the surface of a sample comprises a step for epi-illuminating the surface of the sample, a step for detecting the reflected light reflected from the sample that is epi-illuminated, a step for slant-illuminating the surface of the sample, a step for detecting the reflected light reflected from the sample that is slant-illuminated, a step for detecting the defect on the sample surface based on the respective detected signals of the detected slant illumination reflected light and of the detected epi-illumination reflected light, a step for classifying the detected defect, and a step for supplying the classified result.

Furthermore, in the present invention, a method for inspecting the surface of a sample comprises a step for illuminating a desired region of the sample from the high angle direction with respect to the surface of the sample, a step for detecting the reflected light reflected from the desired region of the sample that is illuminated from the high angle direction, a step for illuminating a desired region of the sample from the low angle direction with respect to the surface of the sample, a step for detecting the reflected light reflected from the desired region of the sample that is illuminated from the low angle direction, a step for detecting the defect on the desired region of the sample based on the respective detected signals of detected reflected light arising from illumination from the high angle direction and of detected reflected light arising from illumination from the low angle direction, a step for classifying the detected defect, and a step for displaying the classified result on a screen.

Furthermore, in the present invention, a method for inspecting the surface of a sample comprises a step for illuminating the sample from the first angle direction with respect to the surface of the sample and for detecting the reflected light reflected from the sample, a step for illuminating the sample from the second angle direction with respect to the surface of the sample and for detecting the reflected light reflected from the sample, a step for detecting the defect on the sample surface based on the first detected signal obtained by detecting the detected reflected light arising from the first angle direction illumination and based on the second detected signal obtained by detecting the detected reflected light arising from the second angle direction illumination, a step for classifying the detected defect, and a step for supplying the classified result.

According to the above-mentioned structure, the defect is discriminated between the very shallow small scratch and the foreign object that occur when the surface of an insulating film or the like of a sample is subjected to CMP process, and further discriminated between the linear large scratch and the foreign object. Furthermore, the small scratch is discriminated between the tire mark, the dimple mark and the rough surface. As the result, it is possible to find out the cause of the defect easily.

These and other objects, features and advantages of the invention will be apparent from the following more particular description of preferred embodiments of the invention, as illustrated on the accompanying drawings.

BRIEF DESCRIPTION OF THE DRAWINGS

FIG. 1 is a schematic structural diagram illustrating the first example of a surface inspection apparatus in accordance with the present invention.

FIG. 20A and FIG. 20B are diagrams for illustrating an example of a scratch configuration classification result in accordance with the present invention.

FIG. 29A and FIG. 29B are diagrams illustrating an example of a behind phase filter shown in FIG. 28.

FIG. 30 is a diagram illustrating an example of an ahead phase filter shown in FIG. 28.

FIG. 32 is an explanatory diagram for describing the principle of the phase difference and luminance generation caused by a scratched portion in accordance with the present invention.

FIG. 33 is an explanatory diagram for describing the principle of the phase difference and the luminance generation caused by a foreign object portion in accordance with the present invention.

FIG. 34 is a discrimination explanatory diagram for discriminating between a scratch and foreign object by means of phase difference technique shown in FIG. 28.

DESCRIPTION OF THE PREFERRED EMBODIMENTS

An embodiment of a surface inspection apparatus and a method for surface inspection designed for stable operation of flattening work process employed in the semiconductor manufacturing process or magnetic head manufacturing process in accordance with the present invention will be described in detail hereinafter with reference to the drawings.

Figure 2A:
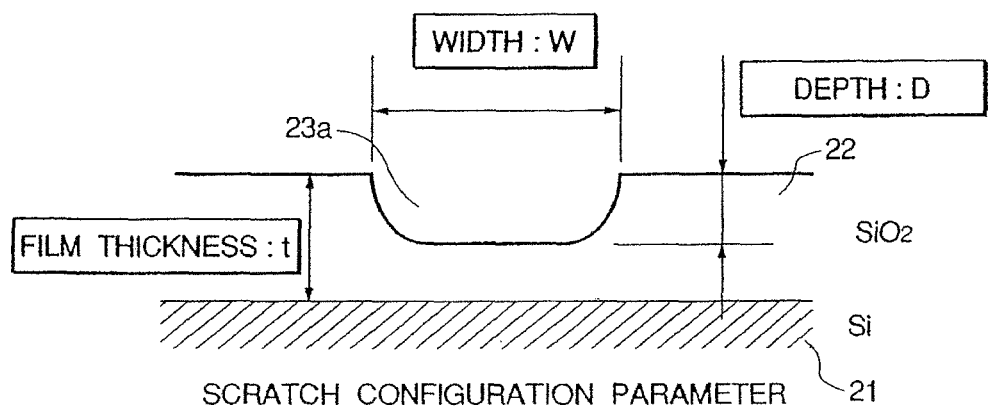
FIG. 2A and FIG. 2B are diagrams illustrating the configuration parameter of the scratch and foreign object that occur on an insulating film respectively in CMP process or the like in accordance with the present invention.
Figure 2B:
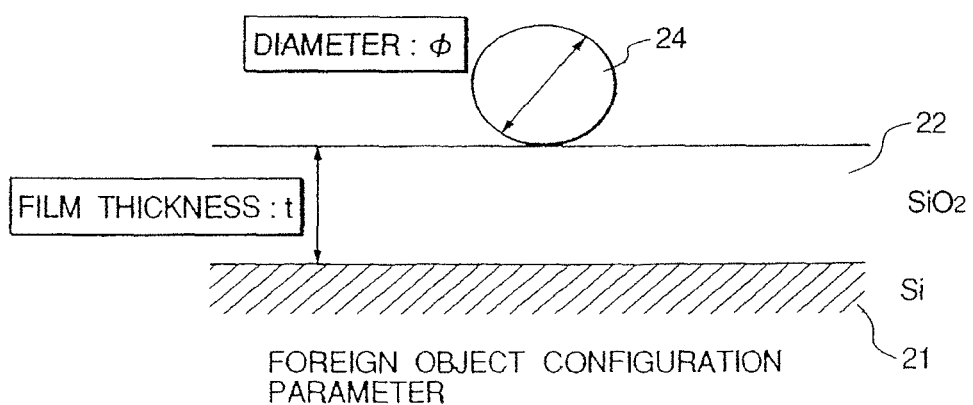

At first, the first embodiment of a surface inspection apparatus and a method for surface inspection in accordance with the present invention will be described. In detail, in the first embodiment, a scratch 23a having a shallow depth formed on a wafer 10 is discriminated from a foreign object 24 adhered on the wafer 10, which have been formed when a $SiO_2$ film (a work target) 22 is formed on a Si wafer 21 and subjected to CMP (Chemical Mechanical Polishing) as shown in FIG. 2A and FIG. 2B. In some cases, there is no Si substrate under the $SiO_2$ film 22 but there is a wiring layer. In CMP process, the surface of the $SiO_2$ film 22 is polished to be flatten. Therefore, a scratch 23a, namely a grinding flaw, is formed on the surface of the $SiO_2$ film 22 as shown in FIG. 2A. Herein, the film thickness of the $SiO_2$ film 22 is denoted by t, the width of the scratch 23 is denoted by W, and the depth of the scratch is denoted by D. W is approximately 0.2 μm to 0.4 μm. D is approximately several nm to the deepest of 100 nm. As described hereinabove, the scratch 23a formed in CMP is characterized by very shallow depth with respect to the width. The size parameter of the foreign object 24 is shown in FIG. 2B. Herein, the foreign object 24 is regarded as a particle having a diameter φ typically. The actual foreign object 24 is not spherical as described in FIG. 2B, but it is true that, though the depth D of the scratch 23a is very shallower as several nm to several tens nm than W of the scratch 23a (approximately 0.2 μm to 0.4 μm), the magnitude of the width of the foreign object 24 is not so different from the magnitude of the height of the foreign object 24. In the present invention, the characteristic dimension ratio of the scratch 23a is utilized as the point.

Aside from the dimension ratio, the scratch is shaped variously. Particularly, CMP involves chemical mechanism and mechanical mechanism mixedly. A scratch 23a that is caused from malfunction of mechanical polishing with a very small grinding mechanism is a minute linear scratch. Though it causes seldom, a linear large scratch 23b having a large depth with respect to the width is formed. However, a scratch 23a and a scratch 23b caused from malfunction of chemical polishing, namely etching polishing mechanism, is dimple-like V-shaped. As described hereinabove, the configuration of the scratch 23 is different depending on the cause of malfunction in polishing. In other words, the detailed classification of the scratch configuration is helpful to find the cause of malfunction. Particularly, in the case that the large scratch 23b is formed often due to foreign object or in the case that a huge scratch 23c is formed, the polishing process is shut down immediately and the countermeasure must be devised.

The first example of a surface inspection apparatus for inspecting the scratch or the like used for realizing the first embodiment will be described with reference to FIG. 1 to FIG. 9. In detail, as shown in FIG. 1, the surface inspection apparatus of the first example is provided with a wafer 10 that is an object to be inspected placed on a stage 15 controllably moved in X-Y direction based on the measured positional coordinate, an illumination optical system 1a comprising a light source 2 having a light source for emitting a light such as Ar laser of wavelength 488 nm (blue wavelength), nitrogen laser, He—Cd laser, or excimer laser (not limited to a laser light source), an optical path switching mechanism 3, and reflection mirrors 4a, 4b, and 4c, a detection optical system 5 comprising a condenser lens 6 and a photoelectric converter 7 having a photomultiplier, CCD camera, CCD sensor, or TDI sensor, a computation processing unit 8 comprising an A/D conversion unit 16 for converting the analog luminance signal supplied from the photoelectric converter 7 to the digital luminance signal, a memory unit 17 for temporarily storing the digital luminance signal obtained from the A/D conversion unit 16, and a comparison computing unit 18, a stage controller 14 for controlling the running of the stage 15 based on the positional coordinate measured by means of the stage 15, and a whole controlling unit 9 for controlling the stage controller 14, for controlling the optical path switching mechanism 3, for controlling the computation processing unit 8, and for receiving the inspection result obtained from the computation processing unit 8.

A light source 2 that emits a light having the short wavelength such as an excimer light source is preferably used to detect discriminatingly between very small foreign object 24 and scratch 23 that occur on an insulating film 22 subjected to CMP. The light emitted from the light source 2 is irradiated on the wafer surface (the surface of the insulating film subjected to CMP) in the normal line direction or approximately in the normal line direction through the reflection mirror 4a and reflection mirror 4c without direct irradiation on the surface of the condenser lens 6. The above-mentioned irradiation is referred to as epi-illumination 12. Otherwise, the light is irradiated on the wafer surface (the surface of the insulating film subjected to CMP) in the slant direction through the reflection mirror 4b by withdrawing the reflection mirror 4a by means of the optical path switching mechanism 3. The irradiation is referred to as slant illumination 11.

In the first example, one light source 2, a plurality of reflection mirrors 4a to 4c, and an optical path switching mechanism 3 are used to realize the epi-illumination and slant illumination, but independent two light sources may be used respectively. The number of reflection mirrors and use of the optical path switching mechanism are optional. Any illumination optical system 1a may be used as long as two illuminations irradiated on the CMP surface subjected to CMP of the insulating film 22 on the wafer 10 in the normal line direction or approximately in the normal line direction and in the slant direction (an angle of approximately 30 degrees or smaller) near the horizontal surface of the wafer respectively are realized.

Next, the detection sequence will be described. The detection is performed twice with switching of the illumination direction on one wafer. In detail, at first, the epi-illumination light 12 is irradiated onto the CMP surface of the insulating film 22 on the wafer 10 without direct irradiation on the surface of the condenser lens 6. As the result, only the scattered light (low order diffracted light component) emitted from the very shallow small scratch 23a and the foreign object 24 that occur due to CMP on the insulating film 22 is converged on the light receiving plane of the photoelectric converter 7 comprising the CCD or TDI sensor by means of the condenser lens 6 in the state that the regular reflected light component generated from the insulating film 22 is removed without generation of stray light reflected from the rough surface on the condenser lens and very small foreign objects adhered on the surface of the condenser lens 6. The output of the photoelectric converter 7 is subjected to A/D conversion by means of the A/D conversion unit 16 to obtain the luminance value S(i) for each defect i, and then written in the memory unit 17 temporarily.

Next, the whole controlling unit 9 controls the stage 15 to thereby switch the irradiation direction by use of the optical path switching mechanism 2, and as the result the same coordinate position on the wafer surface is irradiated with the slant illumination 11. As the result, only the scattered light (low order diffracted light component) emitted from the very shallow small scratch 23a and the foreign object 24 that occur on the insulating film 22 due to CMP is converged on the photoelectric converter 7 by means of the condenser lens 6 in the state that the regular reflected light component generated from the insulating film 22 is removed. Then, the output of the photoelectric converter 7 is A/D-converted by means of the A/D conversion unit 16 to obtain the luminance value T(i) for each defect i, and the luminance value T(i) is stored in the memory unit 17 temporarily.

Next, the comparison computing unit 18 calculates the ratio R(i) of the detected luminance value S(i) for each defect i that has been already obtained during the epi-illumination 12 stored in the memory unit 17 to the detected luminance value T(i) for each defect i that has been obtained during the slant illumination. If the calculated luminance ratio R(i) is larger than the previously set threshold value (the reference value for determination: the discrimination line 20 shown in FIG. 5), then the comparison computing unit 18 discriminates it to be a foreign object 24, on the other hand if the luminance ratio R(i) is smaller than the threshold value, then the comparison computing unit 18 discriminates it to be a very shallow small scratch 23, and the comparison computing unit 18 supplies the result to the whole control unit 9. As described hereinabove, because a scratch 23a formed when CMP is applied is very shallow and small, the feeble stray light generated from the surface of the condenser lens 6 when the epi-illumination light 12 is irradiated on the surface of the condenser lens 6 prevents the discrimination of the scattered light emitted from the scratch 23a if the stray light is received by the photoelectric converter 7. To avoid such problem, the apparatus is structured so that the epi-illumination light 12 is not irradiated on the surface of the condenser lens 6.

In the first example of the present embodiment, the epi-illumination 12 is used for detection at first and the slant illumination 11 is used for detection at second, but the slant illumination may be used at first before the epi-illumination 12 is used for detection. In the structure shown in FIG. 1, the case in which the optical path of the laser emitted from the laser light source 2 is switched by use of the reflection mirror 4a for switching between the epi-illumination and the slant illumination is described, but the case in which a light source for epi-illumination and a light source for slant illumination are provided separately may be employed. Otherwise, the case in which the wavelength of the light emitted from an epi-illumination light source is differentiated from the wavelength of the light emitted from a slant illumination light source and the reflected lights having the respective different wavelengths are detected separately for the epi-illumination and the slant illumination to thereby detect the reflected light of the epi-illumination and the reflected light of the slant illumination simultaneously and separately may be employed.

In the first example of the present embodiment, the case in which the detected luminance value T(i) of the slant illumination 11, namely the luminance value corresponding to the second detection, is A/D converted and then written in the memory unit 17 temporarily is described hereinabove, but the case in which the comparison computing unit 18 refers to the detected luminance value S(i) of the epi-illumination 12 that has been stored already, namely the luminance value corresponding to the first detection, at the time when the detected luminance value T(i) for the second detection is detected to thereby compute the luminance comparison ratio without storing the second detected luminance value T(i) may be employed to realize the present invention.

Next, the discrimination principle involved to realize the above-mentioned embodiment in accordance with the present invention will be described in detail herein under with reference to FIG. 3A to FIG. 3D and FIG. 4. In the present invention, the light flux d is irradiated on one defect in two different directions (for example, epi-illumination 12 and slant illumination 11) for discrimination of the defect. At first, the defect is irradiated with the light flux d in the normal line direction of the wafer surface or approximately in the normal line direction, namely epi-illumination light 12, without direct irradiation on the surface of the condenser lens 6. Next, the defect is irradiated with the light flux d with an angle approximately in the horizontal direction with respect to the wafer surface, namely slant illumination light 11.

Figure 3A:
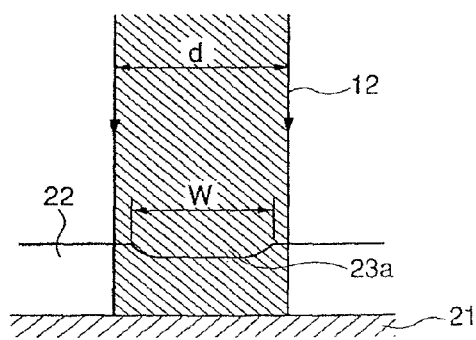
FIG. 3A to FIG. 3D are diagrams illustrating the incident light projection length formed when a light flux d is irradiated on a scratch and a foreign object in accordance with the present invention.
Figure 3B:
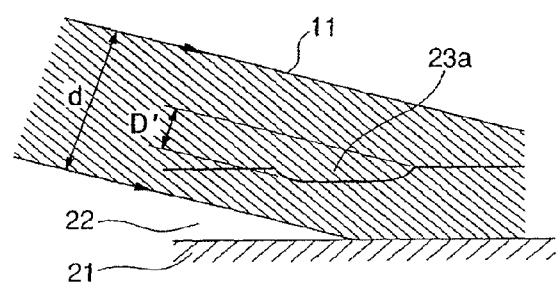
Figure 3C:
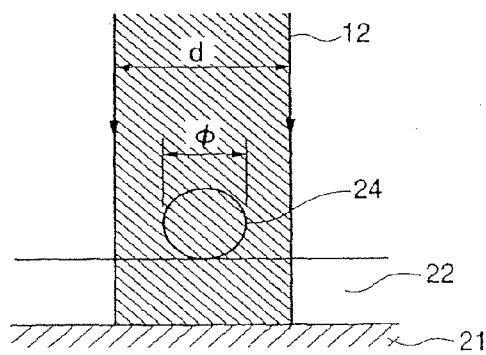
Figure 3D:
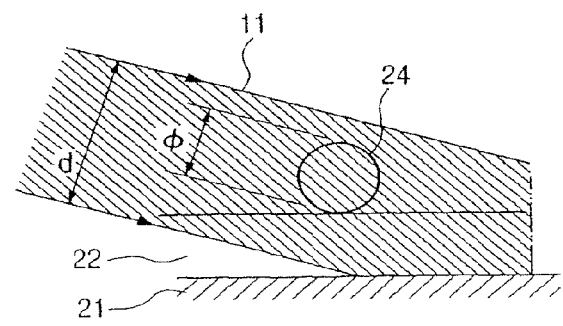
Figure 4:
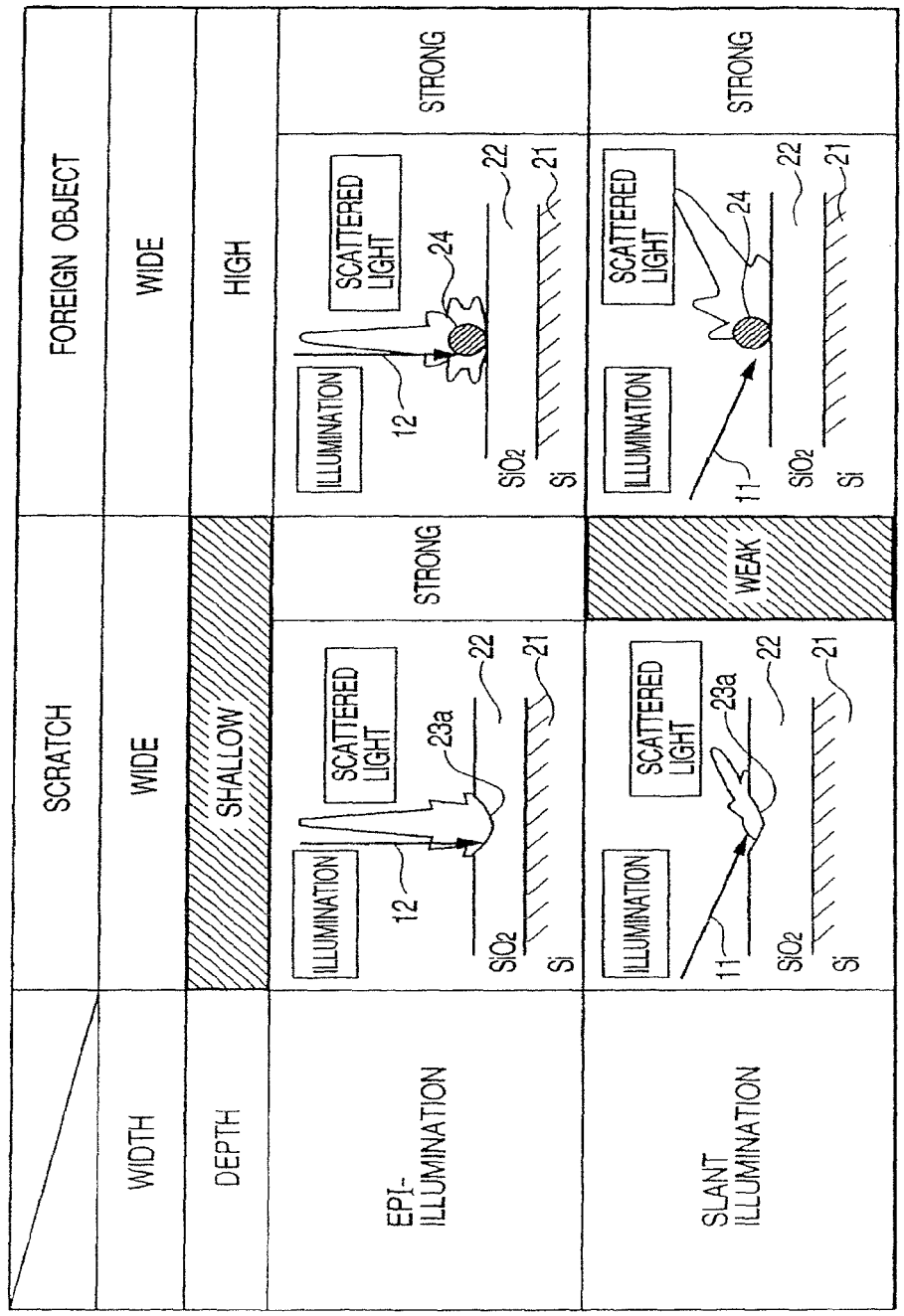
FIG. 4 is a diagram for describing a discrimination principle between the scratch and the foreign object in accordance with the present invention.

The order of the epi-illumination and the slant illumination may be arbitrary. The defect is discriminated by comparing the intensity of scattered lights emitted from the defect 23a or 24 obtained when the light flux d is irradiated in two directions. The intensity of the scattered light from the defect 23a or 24 depends on the light source quantity received by the defect 23a or 24. As shown in FIG. 3A to FIG. D, the light source quantity received by the defect 23a or 24 is approximately proportional to the projected area of the defect in the light source incident direction. In the case of the scratch 23a, the projected area is dependent on the width W for epi-illumination, and the projected area is proportional to D' for the slant illumination. Because the value of the depth D of the scratch is smaller than the value of the width W, the slant illumination projected length D' is extremely smaller than the epi-illumination projected length W'. Therefore, the light source quantity received by the scratch 23a for the slant illumination 11 is smaller than that for the epi-illumination, and as the result the light quantity of the scattered light emitted from the scratch for the slant illumination 11 is smaller than that for the epi-illumination. On the other hand, in the case of the foreign object 24, because the respective projected lengths φ of the slant illumination and the epi-illumination are approximately equal, the light quantity of the scattered light emitted from the foreign object 24 for the slant illumination is almost equal to that for the epi-illumination. Therefore, as shown in FIG. 4, the detected luminance value of the scattered light for the epi-illumination 12 is compared with that for the slant illumination, and if the detected luminance value for the slant illumination 11 is smaller than that for the epi-illumination 12, then the defect is discriminated to be a scratch 23a, and if the detected luminance value for the slant illumination 11 is equal to or larger than that for epi-illumination, then the defect is discriminated to be a foreign object 24.

Aside from the above, because the insulating film (for example, $SiO_2$ film) 22 on which the scratch 23a is formed due to CMP is transparent with respect to the light, the regular reflected light is reflected from the bottom layer including light interference. Particularly in the case of epi-illumination, it is required that the regular reflected light (including light interferential light) from the surface and the bottom layer of the insulating film 22 is guided to the outside of the visual field of the condenser lens 6 so as not to be detected. As a matter of course, also in the case of the slant illumination 11, it is required that the regular reflected light (including interferential light) is guided to the outside of the visual field of the condenser lens 6 so as not to be detected. In the case that a light source for emitting broad band light or white light is used, the problem arising from the light interference between the regular reflected light from the surface of the insulating film 22 and the regular reflected light from the bottom layer is avoided. However, UV light or DUV light is preferably used as the illumination light to obtain the strong scattered light from a small (particularly the depth D is very shallow) scratch 23a or a foreign object 24 on the insulating film 22.

Figure 5:
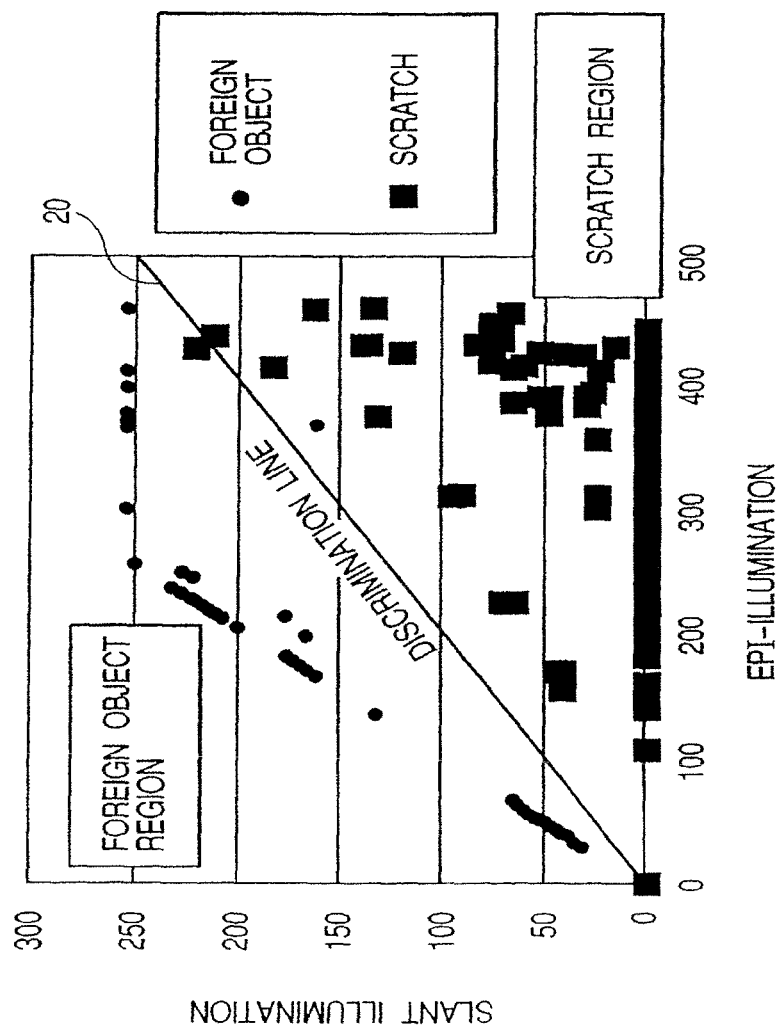
FIG. 5 is a graph for describing a discrimination example between the scratch and the foreign object in accordance with the present invention.

An example of the discrimination result is shown in FIG. 5 graphically. In the graph, the abscissa represents the detected luminance value for the epi-illumination and the ordinate represents the detected luminance value for the slant illumination. In this case, the region under the discrimination line 20 is the region of the scratch 23 and the region above the discrimination line 20 is the region of the foreign 24 in the drawing.

Next, an example of the flow for computation processing by means of the above-mentioned discrimination method will be described with reference to FIG. 6. At first, in step S61, the photoelectric converter 7 detects the luminance signal S(i) for each defect i for the epi-illumination 12 and A/D converts the detected signal, and stores the converted signal in the memory unit 17. Next, in step S62, the photoelectric converter 7 detects the luminance signal T(i) for each defect i for the slant illumination 11 and A/D converts the detected signal, and stores the converted signal in the memory unit 17. Then, in step S63, the comparison computing unit 18 calculates the ratio R(i) of the luminance signal T(i) for each defect i detected for the slant illumination to the luminance signal S(i) for each defect i detected for the epi-illumination stored in the memory unit 17 according to the equation 1 described herein under.

$$R(i)=T(i)/S(i) \quad \text{(equation 1)}$$

Herein, i denotes the identification number given to each defect to evaluate a plurality of defects. Because one defect can be detected as a plurality of defects depending on the size of the light flux d and the photoelectric converter 7 pixel size in some cases, it is required that signals that indicate defects located closely each other are subjected to expansion processing (concatenate processing) so as to be converted to a single signal that indicates one defect. Therefore, the identification number i given to each defect is given to a signal that indicates one defect that has been subjected to concatenate processing.

Furthermore, in step S64, the comparison computing unit 18 discriminates the defect to be a foreign object 24 if the luminance ratio R(i) calculated as described hereinabove is larger than the previously set threshold value (the reference value for determination: the discrimination line 20 shown in FIG. 5), on the other hand the comparison computing unit 18 discriminates the defect to be a scratch 23a if the luminance ratio R(i) is smaller than the threshold value, and the result is supplied to the whole control unit 9. The case in which the detected luminance value T(i) for the slant illumination is divided by the detected luminance value S(i) for the epi-illumination is described in the present example, but the case in which the detected luminance value S(i) for epi-illumination is divided by the detected luminance value T(i) for the slant illumination may be employed. In this case, if the ratio R(i) is larger than the previously set threshold value (the reference value for determination: the discrimination line 20 shown in FIG. 5), then the defect is discriminated to be a scratch 23a, and on the other hand if the ratio R(i) is smaller than the threshold value, then the defect is discriminated to be a foreign object 24.

Next, an example of the location method of the reflection mirror 4c will be described with reference to FIG. 7A to FIG. 7D. The purpose of the method is to prevent the stray light of the dark field detection system and to detect the defect at high sensitivity. The illumination in the direction near the normal line with respect to the plane of the wafer 10 is required for inspection of a scratch 23a as it is obvious from the principle described hereinbefore.

Figure 8:
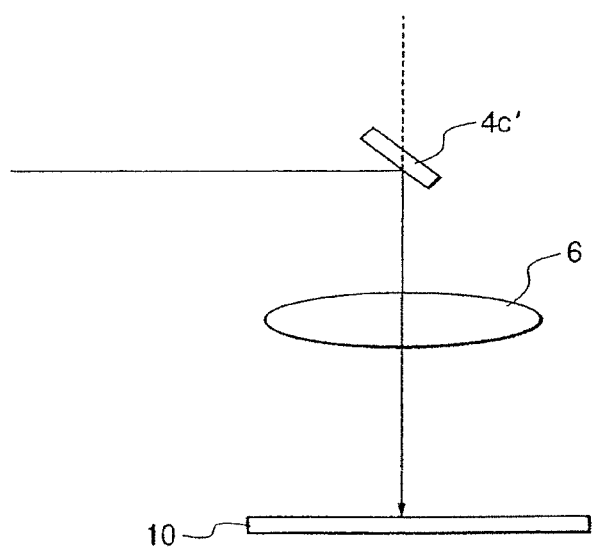
FIG. 8 is an explanatory diagram for describing the conventional epi-illumination technique.

However, in the case of the illumination method (the reflection mirror 4c' is located above the lens 6) as shown in FIG. 8, the incident light passes through the condenser lens 6 and is irradiated onto the wafer 10. As the result, the stray light is generated to cause noise on the detected image. In detail, small polishing marks on the surface of the condenser lens 6 and dusts adhered on the condenser lens 6 cause scattered light, and the scattered light behaves as the stray light. Because of the above, when a feeble scatted light emitted from the defect 23a or 24 is received by the photoelectric converter 7 for observation, the stray light definitely prevents the observation. In other words, the scattered light emitted from a minute scratch 23a cannot be detected discriminatingly from the stray light.

Figure 7A:
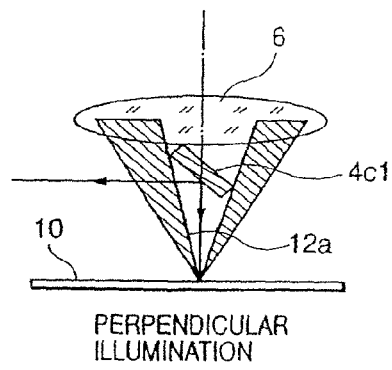
FIG. 7A to FIG. 7D are diagrams illustrating examples of perpendicular irradiation and pseudo perpendicular illumination in accordance with the present invention.
Figure 7B:
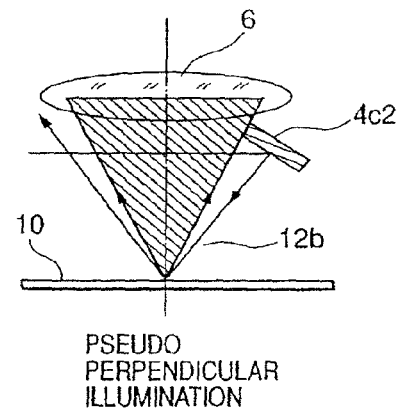

To avoid such problem, in the present invention as shown in FIG. 7A and FIG. 7B, the reflection mirror 4c is located so that the incident light having high intensity is not irradiated onto the surface of the condenser lens 6, and the zero order diffracted light, namely the regular reflected light component reflected from the wafer 10 (the surface of the interlayer insulating film (CMP plane), the surface of underlayered wiring layer, the surface of the scratch 23a, and the surface of the foreign object 24, is not irradiated onto the pupil of the condenser lens 6, namely in the NA.

FIG. 7A showed a method in which the reflection mirror 4c1 is located approximately on the normal line of the wafer 10 between the wafer 10 and lens 6, the epi-illumination light 12a is incident to the reflection mirror 4c1 from the horizontal direction so that the epi-illumination light 12a is not irradiated on the surface of the condenser lens 6 for reflection, and the regular reflected light component reflected from the wafer 10 is reflected on the reflection mirror 4c1 so as not to be incident in the pupil of the lens 6, on the other hand only the scattered light (low order diffracted light component) in the region shaded with slant lines (ring-band shaped in the plane) out of the scattered light (first or higher order diffracted light component) emitted from the scratch 23a or the foreign object 24 is incident in the pupil of the lens 6. The shape of the reflection mirror 4c1 is approximately elliptical. The above-mentioned detection is referred to as the scattered light detection with perpendicular illumination.

Furthermore, FIG. 7B shows a method in which the reflection mirror 4c2 is located between the wafer 10 and the condenser lens 6 outside the NA of the condenser lens 6 and the epi-illumination light 12b is incident to the reflection mirror 4c2 from the horizontal direction so as not to be irradiated on the surface of the condenser lens 6 for reflection, and the regular reflected light component reflected from the wafer 10 is incident outside the pupil of the condenser lens 6, and on the other hand only the scattered light in the region shaded with slant lines out of the scattered light emitted from the scratch 23a or the foreign object 24 is incident in the pupil of the lens 6. In the case that the reflection mirror 4c2 is expanded in the circumferential direction, the illumination light irradiated by the reflection mirror 4c2 is a ring-band illumination. However, as shown in FIG. 7B, if the reflection mirror 4c2 is limited partially, the illumination light becomes a partial illumination in the ring-band illumination. Such detection is referred to as the scattered light detection with pseudo perpendicular illumination.

Figure 7C:
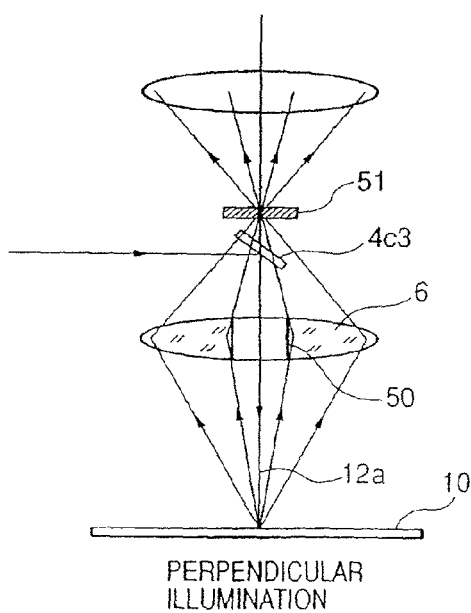

FIG. 7C shows a method in which the reflection mirror or a half mirror 4c3 is located above the condenser lens 6 having an aperture 50 at the center thereof, the perpendicular illumination light 12a reflected on the half mirror 4c3 is not irradiated on the surface of the condenser lens 6 but passes through the aperture 50 so as to be irradiated on the CMP surface of the insulating film on the wafer 10, the regular reflected light component reflected on the wafer 10 is shaded by use of a space filter 51 located on the Fourier transformation plane, and the scattered light obtained through the condenser lens 6 out of the scattered light emitted from the scratch 23a or the foreign object 24 is received by the photoelectric converter 7.

Figure 7D:
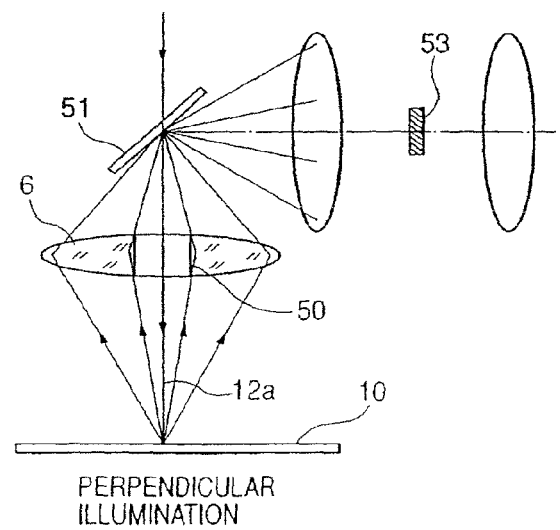

Furthermore, FIG. 7D shows a method in which the epi-illumination light 12a passes through a half mirror 52, passes through an aperture 50 of the condenser lens 6, and is irradiated on the CMP surface of the wafer 10, the regular reflected light reflected on the wafer 10 is shaded by use of a space filter 53 located on the Fourier transformation plane, and only the scattered light obtained through the condenser lens 6 out of the scattered light emitted from the scratch 23a or the foreign object 24 is reflected by the half mirror 52 and received by the photoelectric converter 7 in the same manner as used in the method shown in FIG. 7C.

Figure 13A:
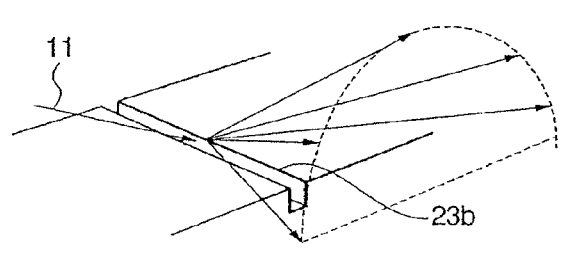
FIG. 13A and FIG. 13B are diagrams illustrating the diffracted light distribution diffracted when a linear large scratch is illuminated in accordance with the present invention.
Figure 13B:
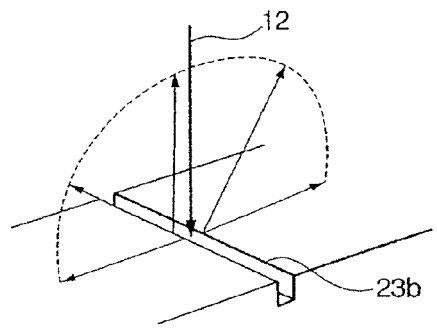

As described hereinabove, in the case of the method described referring to FIG. 7C and FIG. 7D, the aperture 50 is formed at the center of the condenser lens 6 so that the perpendicular illumination and the scattered light detection in the perpendicular direction are made possible as in the case of FIG. 7A without generation of the stray light from the surface of the condenser lens 6. Therefore, the scattered light emitted from the edge of a very shallow scratch 23a can be received relatively evenly by the photoelectric converter regardless of the direction of the scratch 23a in the horizontal plane, and the even detected luminance value is obtained. Furthermore, as shown in FIG. 13B, the perpendicular illumination is more preferable than the pseudo perpendicular illumination to obtain the diffracted light that is strongly directional in the right angle direction with respect to the large scratch 23b, namely a linear pattern.

Aside from the above, in the case of the scattered light detection with perpendicular illumination shown in FIG. 7A, the incident light passes under the lens 6 and will not be irradiated on the surface of the condenser lens 6 apparently, and the stray light will not be generated. Furthermore, because the regular reflected light reflected on the wafer 10 is reflected on the reflection mirror 4c1, the regular reflected light will not be irradiated in the pupil of the condenser lens 6. Furthermore, it is true for the perpendicular illumination shown in FIG. 7C and FIG. 7D. Furthermore, also in the case of the scattered light detection with pseudo perpendicular illumination, the incident light will not pass the condenser lens 6 apparently. Because the reflection mirror 4c2 is located outside the NA of the condenser lens 6, the regular reflected light component reflected on the wafer 10 is not irradiated in the pupil of the condenser lens 6. As described hereinabove, in any method, the epi-illumination is realized so that the incident light that has a strong light intensity and is apt to generate the stray light is not irradiated on the surface of the condenser lens 6, and the regular reflected light reflected from the wafer is not incident to the condenser lens 6. Therefore, the stray light is not generated and it is possible to obtain the detected image having high S/N ratio from the scratch 23a and the foreign object 24 that occur on the CMP surface of the interlayer insulating film 22 subjected to CMP. Because the interlayer insulating film 22 is transparent with respect to the light, the light regularly reflected on the bottom layer returns from the bottom layer when the epi-illumination is irradiated. However, because the regularly reflected light is not irradiated in the NA of the lens 6 as described herein under, the regular reflected light does not adversely affect the detection of the scattered light emitted from the scratch 23a and the foreign object 4, and it is possible to detect the scratch 23a and the foreign object 24 by mean of the signal obtained from the photoelectric converter 7.

Furthermore, using of the epi-illustration 12a and 12b together with the slant illumination 11 improves the detection sensitivity in comparison with the case in which only the slant illumination 11 is used, because the strong light component of the scattered light intensity distribution from the scratch 23a is easily received in addition to the reason of solution of the stray light problem. The reason is that the low order diffracted light component out of the scattered light intensity from the scratch 23a is relatively strong. In other words, by irradiating the light approximately in the normal line direction with respect to the wafer plane, the low order diffracted light is reflected from the wafer 10 and easily converged by the condenser lens 6.

As the result, it is possible to detect the scratch 23a with higher sensitivity in comparison with the case in which only the slant illumination 11 is used. As described hereinabove, it is possible to realize the high sensitivity detection of the scratch 23a by using only the perpendicular illumination 12a or the pseudo perpendicular illumination 12b.

In the case that the reflection mirror 4c1 is located in the NA of the condenser lens 6, by forming the shape of the reflection mirror 4c1 approximately elliptical so as not to affect adversely the image forming characteristic of the lens 6, the scattered light in the region shaded with slant lines (the ring-band region in the plane) shown in FIG. 7A is converged by the condenser lens 6 to form an image. However, in the case that the reflection mirror 4c1 located in the NA of the condenser lens 6 adversely affects the image-forming characteristic, a mechanism that is served to withdraw the reflection mirror 4c1 outside the NA when the perpendicular illumination is irradiated is required. It is required that dust generated from the defect inspection apparatus is reduced to the extremely low level in the semiconductor inspection. From this view point, it is not preferable that the movable mechanism is located above the wafer. However, in such case, the pseudo perpendicular illumination 12b may be used. In the case of the pseudo perpendicular illumination 12b, the reflection mirror 4c2 will not adversely affect the image forming characteristic because the reflection mirror 4c2 is located outside the NA, and it is not required that a withdrawing mechanism is provided separately.

Furthermore, in the case that a surface inspection apparatus for inspecting the scratch in accordance with the present invention is used as a foreign object inspection apparatus with only the slant illumination, the perpendicular illumination is not necessary. Therefore, it is possible that the reflection mirror 4c1 shown in FIG. 7A is withdrawn so that the entire NA of the condenser lens 6 is used, and the scattered light emitted from the foreign object is effectively converged and received by the photoelectric converter 7.

However, to reduce the generation of dust without withdrawal of the reflection mirror 4c1, the pseudo perpendicular illumination 12b may be used as the perpendicular illumination of the surface inspection apparatus though the scratch detection accuracy level is slightly lowered. Furthermore, in the case that the method shown in FIG. 7C and FIG. 7D is used as the perpendicular illumination, the surface inspection apparatus can be used as the foreign inspection apparatus with only the slant illumination without using the perpendicular illumination. In the case that the surface inspection apparatus is used as the foreign object inspection apparatus with only the slant illumination, because it is required to shade the diffracted pattern based on the diffracted light from the periodical wiring pattern when the foreign object on a memory cell, on which the periodical wiring pattern has been formed, is to be detected, the space filters 51 and 53 may be replaced with liner space filters.

Figure 9:
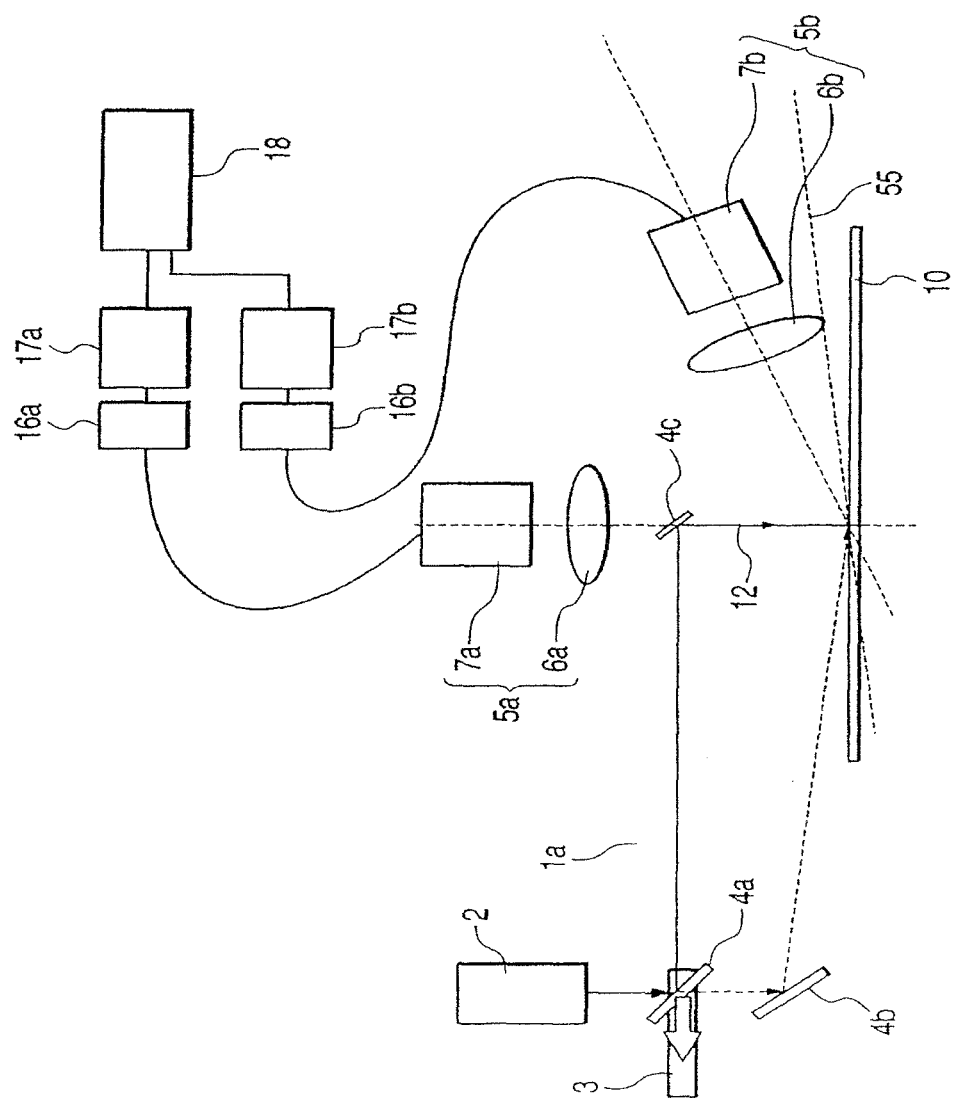
FIG. 9 is a schematic structural diagram illustrating a modified example different from the first example shown in FIG. 1 in that the modified example involves two direction light receiving.

The case in which one detection optical system 5 is used is described in the first example of the present embodiment, but the case in which a plurality of detection optical systems 5a and 5b are used as shown in FIG. 9 may be employed. Particularly, the detection optical systems 5a and 5b are located in the direction that is suitable for detecting the strongest scattered light emitted from the defect 23a or 24 for each irradiation direction to realize the detection at higher sensitivity. For example, as shown in FIG. 9, a lens 6a and photoelectric converter 7a of the detection optical system 5a for epi-illumination are provided in the wafer normal line direction, in which direction the scattered light intensity is very strong. The location of the lens 6a is applicable to the perpendicular illumination 12a and the pseudo perpendicular illumination 12b.

As the detection optical system 5b for the slant illumination, a condenser lens 6b and a photoelectric converter 7b are provided in the regular reflection direction of the slant incident light, in which direction the scattered light intensity is very strong. However, as for the detection optical system 5b comprising the lens 6b and the photoelectric converter 7b, it is required not to converge the regular reflected light component reflected from the wafer 10. Therefore, it is not preferable that the detection optical system 6b is provided in the regular reflected light emergent direction 55, but it is preferable that the detection optical system 6b is located at the place so that the regular reflected light component is irradiated outside the NA of the condenser lens 6b. In the case of the present example, because two detection optical systems 5a and 5b are provided, two A/D conversion units 16a and 16b and two luminance memory units 17a and 17b are provided. As a matter of course, one memory unit 17, for example one RAM, may be used by storing the data separately in the different addresses in the memory unit 17.

In the structure shown in FIG. 9, a light source for the epi-illumination and a light source for the slant illumination may be provided separately. Furthermore, the wavelength of the light emitted from the light source for the epi-illumination may be differentiated from that for the slant illumination, the reflected light from the wafer surface is detected separately for respective wavelengths. As the result, the epi-illumination and the slant illumination are irradiated simultaneously, and the reflected light of the epi-illumination and the reflected light of the slant illumination are detected simultaneously and separately.

The second example of a surface inspection apparatus for detecting the scratch or the like in accordance with the present invention will be described with reference to FIG. 10 to FIG. 12D. The second example of the present embodiment is different from the first example in the detection optical system 5. In detail, the detection optical system 5 is characterized by comprising a high angle detection optical system 5a, a medium angle detection optical system 5c, and a low angle detection optical system 5b. The structure for placing the substrate table 51 on which a wafer 10, namely an object to be inspected, is fixed by means of, for example, vacuum-suction on the stage 15 is omitted in the first example. In the second example, the stage 15 comprises a linearly moving stage 15a and a rotationally moving stage 15b. In other words, any stage 15 may be used as long as a wafer 10 is transferred so that the arbitrary position on the wafer 10 is irradiated with a light. Furthermore, as for the computation processing unit 8, the A/D conversion unit 16 and the memory unit 17 are structured correspondingly to the detection optical systems 5a to 5c. The illumination optical system 1a is structured as in the case of the first example. In other words, as for the perpendicular illumination, the illumination light reflected on the reflection mirror 4a is reflected on the reflection mirror 4d, passes through a half mirror 52, passes through an aperture 50 formed on a condenser lens 6a as shown in FIG. 7D, and is irradiated on the CMP surface of the wafer 10 as the light flux d. The regular reflected light generated from the wafer 10 is shaded with a space filter 53, the low order diffracted light emitted from the edge of a scratch 23a and a foreign object 24 is converged by a condenser lens 6a of the high angle detection optical system 5a. The converged diffracted light is received by a photoelectric converter 7a, and the higher order diffracted light is detected by the medium angle detection optical system 5c. As a matter of course, the perpendicular illumination 12 having the structure shown in FIG. 7A, FIG. 7B, or FIG. 7C may be used. The slant illumination 11 is reflected on the reflection mirror 4b and irradiated on the CMP surface of the wafer 10 as the light flux d. The regular reflected light generated from the wafer 10 is not detected, but the diffracted light emitted particularly from the foreign object 24 is detected by the detection optical systems 5a to 5c.

Figure 11A:
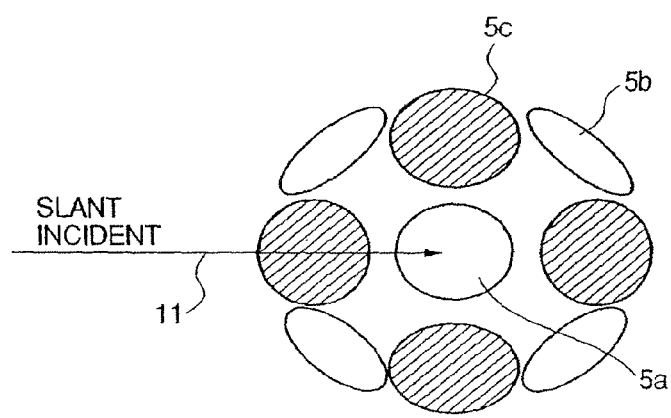
FIG. 11A and FIG. 11B are a plan view and a front view of a multiple direction detection optical system respectively shown in FIG. 10.
Figure 11B:
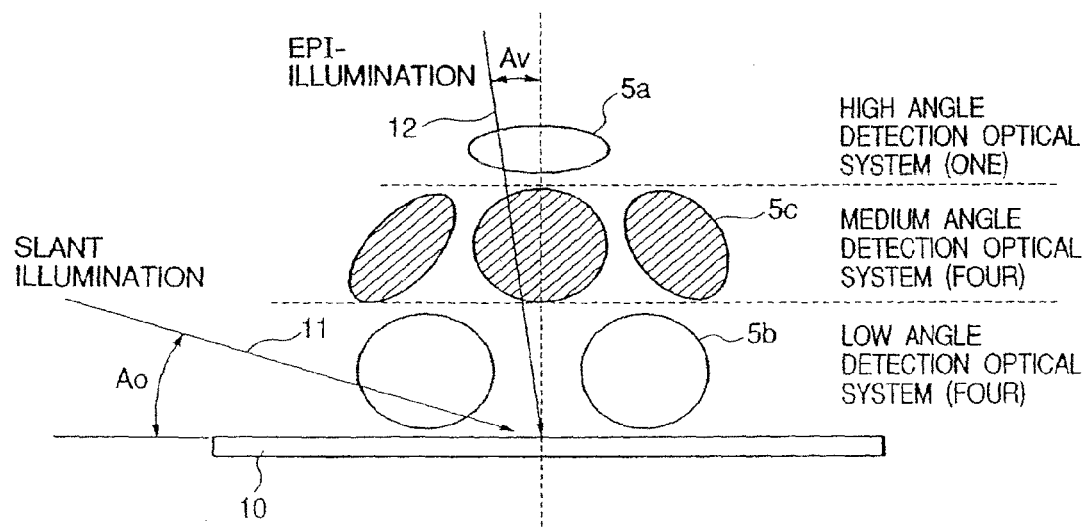

Next, the detection optical system of the second example will be described in detail with reference to FIG. 11A and FIG. 11B. In detail, the detection optical system comprises one high angle detection optical system 5a, four medium angle detection optical systems 5c, and four low angle detection optical systems 5b including condenser lenses 6a to 6i and photoelectric converters 7a to 7i. Photomultipliers are used as the photoelectric converters 7a to 7i in the present example. Nine photomultipliers are used and located in the dome arrangement as shown in FIG. 11A and FIG. 11B. The photomultipliers 7a to 7i are provided with condenser lenses 6a to 6i respectively. The case in which the condenser lenses 6a to 6i and the photomultipliers 7a to 7i are used for the detection optical system is described in the present example, but, for example, the case in which CCD camera or TDI sensor is used may be employed to form an image. Furthermore, the number of photoelectric converters 7a to 7i is by no means limited to 9. The outputs of the photoelectric converters 7a to 7i are written in the memory units 17a to 17i by way of ND conversion units 16a to 16i. Simultaneously, the coordinate data of the wafer 10 obtained from the stage controller 14 is written in the memory units 17a to 17i. The coordinate data and the luminance data are transmitted to a comparison computing unit 18. In the case that the entire surface of the wafer is inspected, it is required to write the coordinate data and the luminance data in the memory units 17a to 17i as described hereinabove. However, in the case that the specified coordinate position is inspected fixedly, the coordinate data is not necessarily required. The coordinate data and the luminance data are not necessarily stored in the same memory units 17a to 17b in the form of a pair, and may be stored in different memory units. Furthermore, the coordinate is not necessarily stored, but, for example, the identification number given to the detected defect may be stored instead of the coordinate. Any method may be employed as long as the detection luminance data for the slant illumination and the detection luminance data for the epi-illumination of the same defect are correlated each other. In the present example, the data of the same coordinate position or on the position near to the coordinate position out of the data of two set of the epi-illumination and the slant illumination are recognized as the luminance data of the same defect by using the coordinate data. Thereby, the luminance value S(i) of the epi-illumination 12 is compared with the luminance value T(i) of the slant illumination 11.

As shown in FIG. 11A and FIG. 11B, one detection optical system 5a is located in the incident direction of the epi-illumination 12 (having the angle Av from the normal line direction with respect to the wafer plane. Preferably, the angle Av is 0). This detection optical system 5a is referred to as high angle detection optical system 5a. Four detection optical systems 5c and four detection optical systems 5b are located in the order from the position near the high angle detection optical system 5a to the position near the wafer plane, and the former is referred to as the medium angle detection optical system 5c and the latter is referred to as the low angle detection optical system 5b. The case in which total nine detection optical systems are used is described in the present example, but the number of detection optical systems is by no means limited to 9 as the means for realizing the present invention.

Figure 12B:
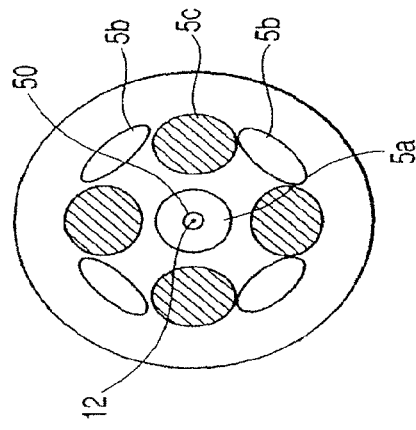
FIG. 12A to FIG. 12D are diagrams illustrating the second example that uses the multiple direction detection optical system shown in FIG. 10.
Figure 12D:
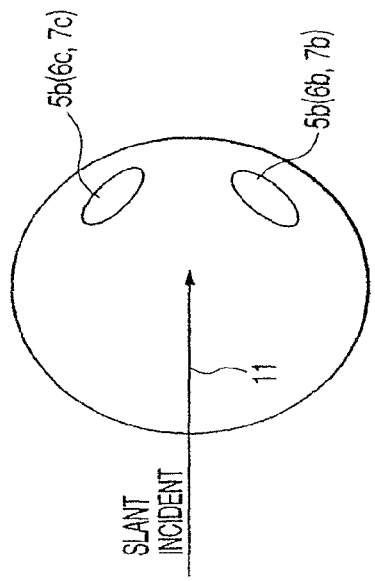
Figure 12A:
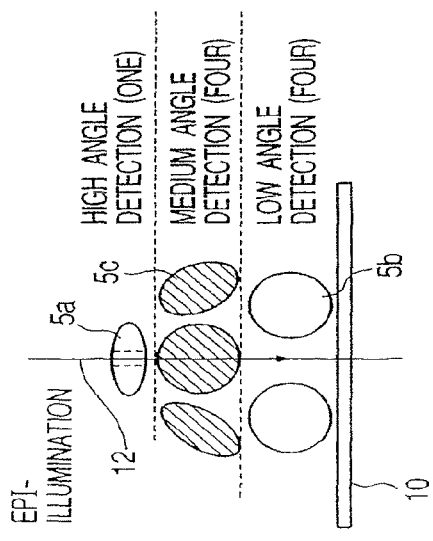

In the present example, the case in which all the nine detection optical systems 5a to 5c are used as the light receiving means when the epi-illumination is applied as shown in FIG. 12A and FIG. 12B, and the sum of the received light luminance of the nine photoelectric converters 7a to 7i is used as the received light luminance when the epi-illumination 12 is applied is described. However, it is not necessarily required to use all the nine detection optical systems to obtain the received light luminance with the epi-illumination, but only the high angle detection optical system 5a, or only medium angle detection optical system 5c, or the sum of received light quantity of the high angle detection optical system 5a and the medium detection optical system 5c may be used. Particularly for detection of the low order diffracted light emitted from the scratch 23a and foreign object 24 with the epi-illumination, only the medium angle detection optical system 5c may be used instead of the high angle detection optical system 5a. At that time, because the regular reflected light (zero order diffracted light) is not incident on the NA of the medium angle detection optical system, the sum of light quantity of the medium angle detection optical system 5c may be calculated simply. As described hereinabove, various combinations may be used selectively, but in the present example, the sum of the received light quantity of all the detection optical systems 5a to 5c is used so that the defect detection sensitivity is maximized, that is, so that so-called high NA (Numerical Aperture) is realized. However, because most of diffracted light emitted from the scratch 23a and the foreign object 24 is detected by means of the high angle detection optical system 5a and the medium angle detection optical system 5c, it is preferable to use the sum of the received light quantity of both detection optical systems.

Figure 12C:
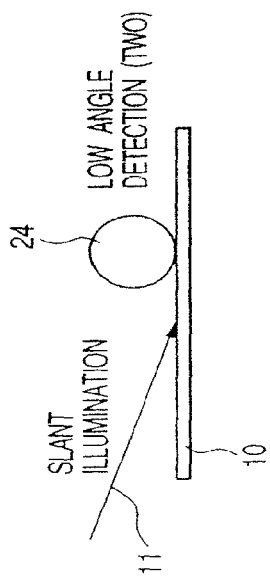

As the light receiving means that is used when the slant illumination 11 that makes an angle of Vo with respect to the wafer plane is irradiated, two low angle light receivers 6b, 7b: 6c, 7c located on the side near to the regular reflection direction reflected from the wafer when the slant illumination is incident as shown in FIG. 12C and FIG. 12D are used. The sum of the received light luminance of these two receivers is used as the received light luminance obtained when the slant illumination 11 is irradiated. The light receiver to be used is by no means limited to the two low angle light receivers. In the present example, the detection optical system (condenser lens 6b and photoelectric converter 7b) 5b that is located in the direction where the strong scattered light distribution intensity is detected is merely selected without receiving the regular reflected light in order to realize high sensitivity detection as described referring to FIG. 9. From the view point of discrimination, it is important that two directional illuminations are used and the respective scattered light intensities are detected, and the direction of the light receiving means 5b is not so important. The direction of the detection optical system (condenser lens 6, and photoelectric converter 7) 5 may be determined depending on the level of requirement for discriminating between a small foreign object 24 and scratch 23a. In the case that the high angle detection optical system 5a is used as the detection optical system 5, it is required not to generate stray light from the surface due to the epi-illumination.

The example of the method for discriminating between the foreign object 24 and the scratch 23a by use of two directional illuminations described hereinabove is based on the fact that the depth of the scratch 23a is characteristically shallow.

However, as described hereinabove, in some cases a large foreign object comes in a CMP apparatus from the external and causes a very deep flaw though it occurs seldom in the case of CMP. In the case that a large foreign object comes in during polishing and the large foreign object, not a very small grinding abrasive grain, causes the scratch, a scratch 23b having a large depth with respect to the width W is formed. In the case of the scratch 23b having a deep depth as described hereinabove, the scratch is mis-recognized to be a foreign object 24 through it is really a scratch 23. As the result, the huge scratch that should be recognized is not recognized.

Then, the second embodiment for recognizing discriminatingly between a deep scratch 23b and a foreign object 24 will be described hereinafter. In the first embodiment, because the ratio R(i)=T(i)/S(i) is large for the foreign object 24 and also for the deep scratch, the large scratch 23b having deep depth and also the foreign object 24 are detected together in step S64 of the discrimination processing flow shown in FIG. 6. Then, the purpose of the second embodiment is to discriminate between the large scratch 23b and the foreign object 24 correctly. Herein, S(i) denotes the luminance data for each defect after concatenate processing of the first inspection with the epi-illumination 12. T(i) denotes the luminance data at the same coordinate value i out of data for each defect after concatenate processing of the second inspection with the slant illumination 11.

The discrimination is based on the fact that the scratch 23b having a deep depth D with respect to the width W has a long length inherently. The reason is that the wafer is polished with rotation in CMP process and the deep scratch will not have a short length differently from the nick having a local deep concave. The second embodiment of the present invention is based on the above-mentioned certainty, a linear long defect is further classified as the large scratch 23b out of defects recognized as the foreign object 24 in step S64 shown in FIG. 6. At that time, the defect is classified based on the principle shown in FIG. 13A and FIG. 13B. When a light flux 12 is irradiated from the normal line direction onto a large scratch 23b with linear pattern as shown in FIG. 13B, the diffracted light exhibits a distribution having very strong directionality in the right angle direction of the linear pattern 23b. FIG. 13A shows a case in which a light flux 11 is irradiated with inclination from the normal line direction onto the large scratch 23b having a linear pattern, and shows the principle of space filtering method for removing the linear diffracted light pattern arising from wiring patterns repeatedly arranged regularly with irradiation of the slant illumination used in the foreign object inspection apparatus. In the present invention, the strong directionality of the diffracted light emitted from the large scratch 23b with irradiation of the perpendicular illumination 12 is recognized as shown in FIG. 13B. Thereby, the defect is recognized as a large scratch 23b having a linear pattern and not the foreign object 24.

Figure 14:
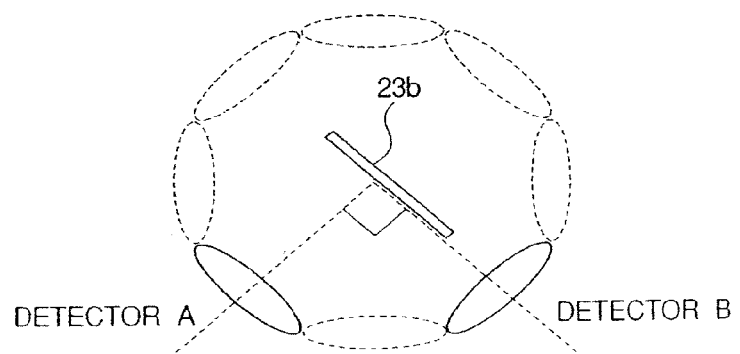
FIG. 14 is a diagram illustrating the discrimination principle by means of reception of the light diffracted from the linear large scratch in accordance with the present invention.

The discrimination principle between the large scratch 23b and the foreign object 24 will be described with reference to FIG. 14 and FIG. 15. At first, for example, the epi-illumination 12 is applied onto the wafer 10, and the computation processing unit 8 selects the detection optical system A having the highest luminance from among a plurality (eight) of low angle and medium angle detection optical systems 5b and 5c (photoelectric converters 7b to 7i) in step S65. Next, the computation processing unit 8 refers to the luminance value Sb(i) of the detection optical system B that is orthogonal to the A detection optical system in step S66, and compares the luminance value Sa(i) of the detection optical system A with the luminance value Sb(i) of the detection optical system B to thereby calculate the luminance ratio (Sa(i)/Sb(i)) in step S67. Next, the computation processing unit 8 compares the calculated luminance ratio (Sa(i)/Sb(i)) with the previously set value (threshold value), and classifies the luminance ratio larger than the threshold value as a large scratch 23b, namely linear defect, and the luminance ratio smaller than the threshold value as a foreign object 24, namely non-linear defect, or a small scratch 23a.

As described hereinabove, according to the second embodiment, because the computation processing unit 8 discriminates the large scratch 23b from the foreign object 24 or the small scratch 23a, the combination of the first embodiment and the second embodiment is capable of discriminating between the small scratch 23a, foreign object 24, and large scratch 23b.

Figure 16:
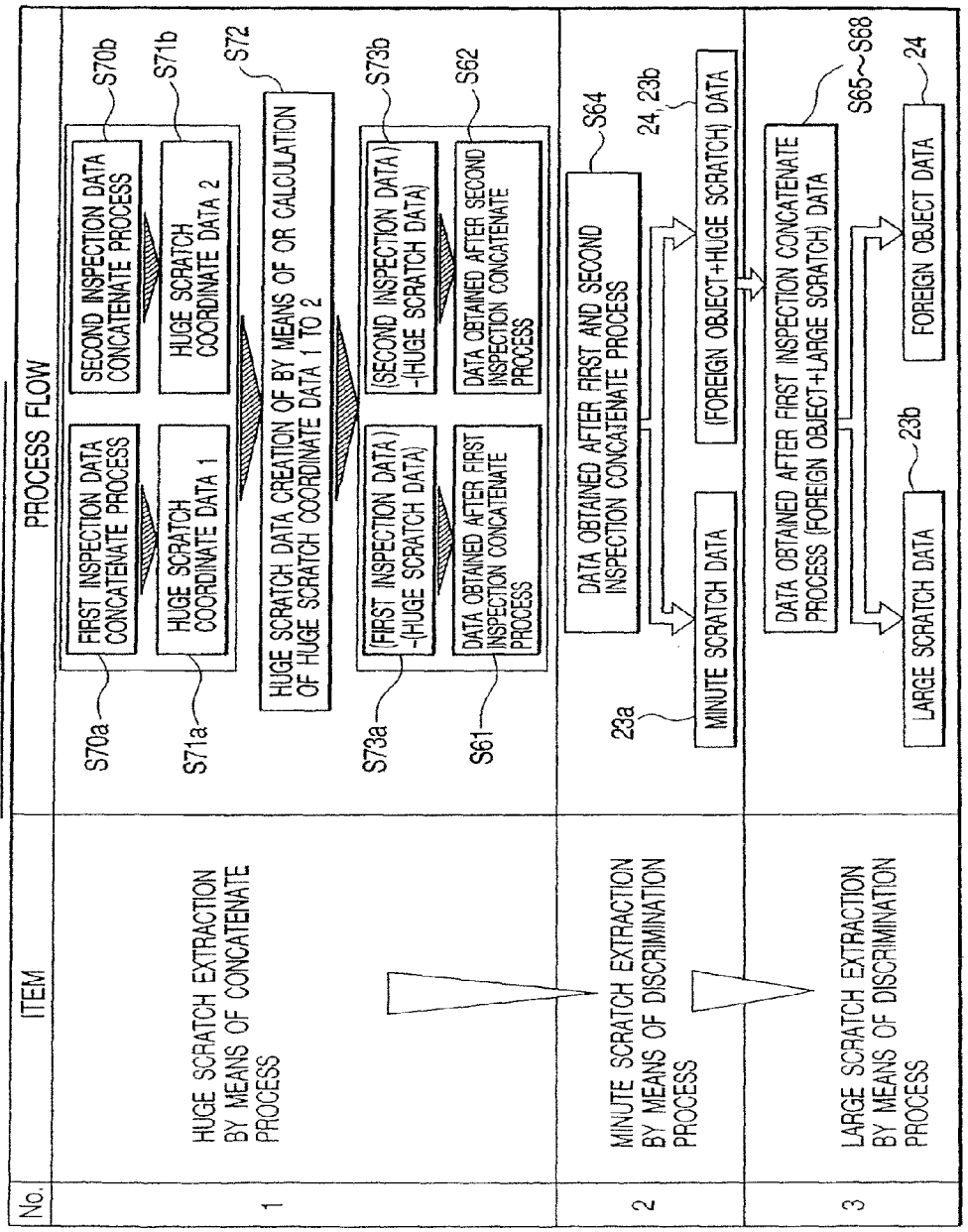
FIG. 16 is a diagram for describing an example of the whole flow of a discrimination algorithm in accordance with the present invention.

Next, the third embodiment used to discriminatingly recognize the deep scratch 23b from the foreign object 24 will be described hereinafter. In detail, in the third embodiment, the mechanism for extracting the long huge scratch 23c, for example, a huge scratch 23c that extends across a wafer, is incorporated as shown in FIG. 16. The long and huge scratch 23c that can be found visually can be extracted easily only by evaluating the length after concatenate processing by means of the computation processing unit 8. However, the function of the present invention will not be adversely affected without the processing for extracting the huge scratch 23c.

At first, in the algorithm in the computation processing unit 8, each inspection data for two incident directions (first inspection: epi-illumination 12, second inspection: slant illumination) is subjected to concatenate processing in steps S70a and S70b to thereby obtain the huge scratch coordinate data 1 and 2 in steps S71a and S71b. The concatenate processing involves the expansion processing for recognizing the data arising from positions located closely each other as the data of one defect. For example, if signals that indicate defects around the pixel are detected in 3×3 pixels, then the expansion processing for giving a signal that indicates to the center pixel is repeated a plurality of times to thereby concatenate defects that are located closely each other. One defect can be extracted as a plurality of defects erroneously due to the spot size and pixel size unless the concatenate processing is introduced. Next, the computation processing unit 8 refers to the coordinate data 1 and 2 that indicate the defect after concatenate processing (for example, refers to the logical sum of the signal that indicates the defect) in step S72 to thereby extract a long defect as a huge scratch 23c (prepare the huge scratch data). Furthermore, the computation processing unit 8 refers to the number of the coordinate data 1 and 2 that indicate defects concatenated in the concatenate processing in step S72 to thereby extract a defect having a large area as a huge scratch 23c (prepare the huge scratch data).

Next, the computation processing unit 8 removes the data that is recognized as the data of the huge scratch from each of the first inspection data and the second inspection data in steps S73a and S73b respectively to thereby obtain the concatenated first inspection data and second inspection data in steps S61 and S62 respectively, and the obtained data is stored in the memory unit 17.

Figure 6:
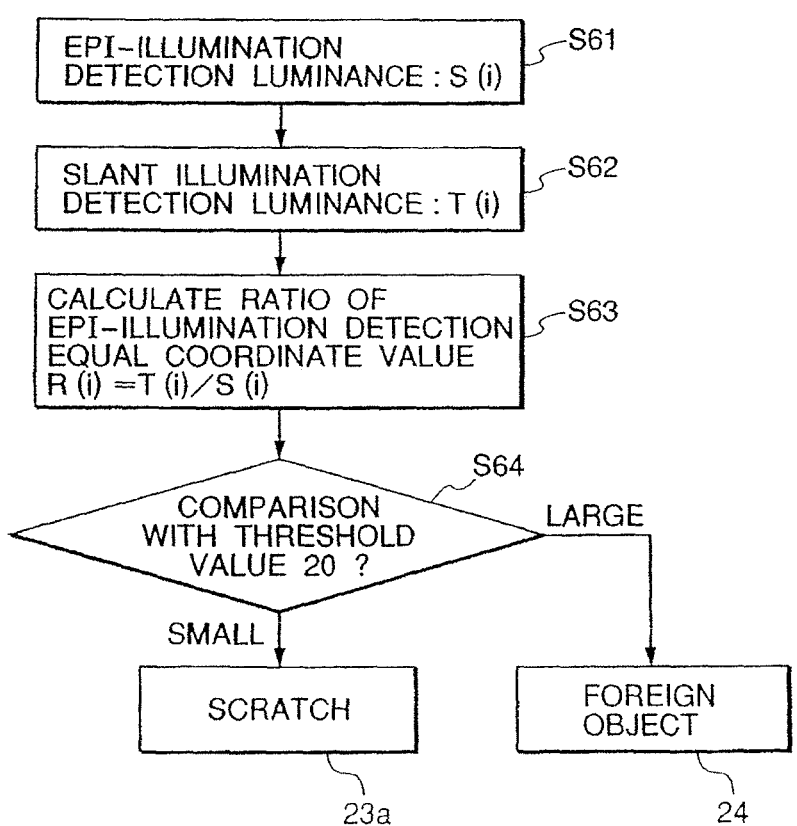
FIG. 6 is a flow chart for describing an example of discrimination process flow between the scratch and the foreign object in accordance with the present invention.

Next, the comparison computing unit 18 discriminates between the scratch 23a and the foreign object 24 or large scratch 23b with two directional illustrations shown in FIG. 6 in step S64 by use of the concatenated first inspection and second inspection data obtained and stored in the memory unit 17.

Figure 15:
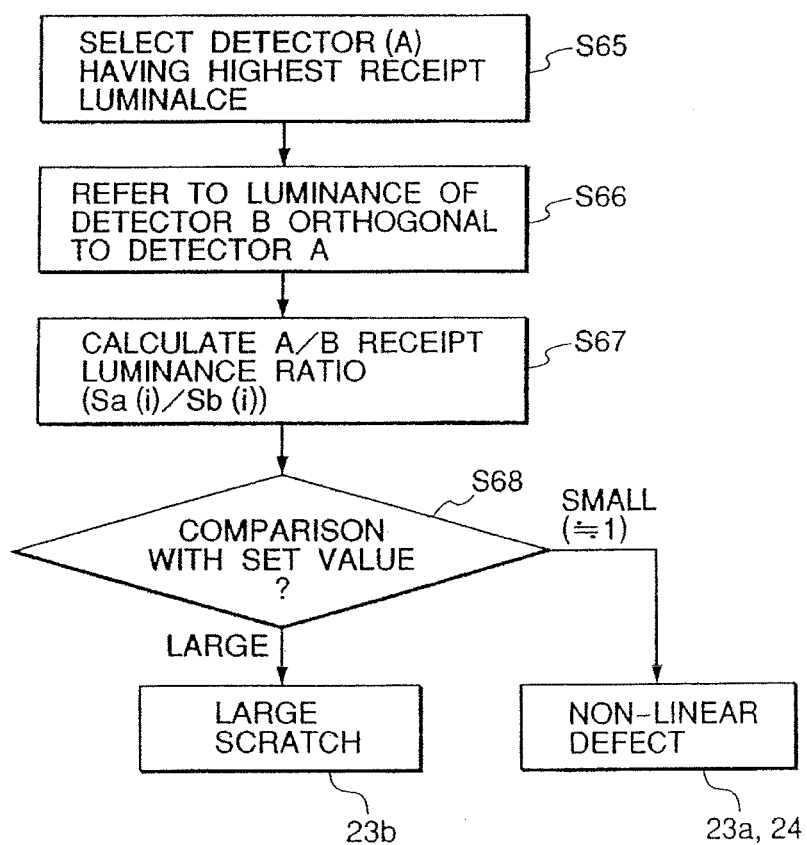
FIG. 15 is a flow chart for describing an example of a discrimination process flow for discriminating between a large scratch and a non-linear defect in accordance with the present invention.

Next, the computation processing unit 8 discriminates the data of the large scratch 23b from the data discriminated as the data of the foreign object 24 or large scratch 23b in steps S65 to S68 as shown in FIG. 15. This discrimination processing will be described in detail with reference to FIG. 17. Eight photomultipliers 7b to 7i of the low angle detection optical system 5b and medium angle detection optical system 5c are used in the discrimination processing. In this case, the solid angle of the low angle is different from that of the medium angle, and the solid angle difference results in the sensitivity difference between the low angle and the medium angle. The product characteristic of the photomultipliers 7b to 7i is often different individually. Therefore, the sensitivity balance between eight photomultipliers must be adjusted. To adjust the balance, the applied voltage on the each of photomultipliers 7b to 7i is changed previously to adjust the sensitivity. For very fine sensitivity balance adjustment, it is effective that the gain is set to each of the photomultipliers 7b to 7i and the detected luminance is compensated by means of software or hardware. However, the intensity compensation by means of gain is needed not necessarily. Next, the computation processing unit 8 sums up the luminance obtained from the opposite photomultipliers by use of the data that has been subjected to compensation of sensitivity balance between the photomultipliers in step S75. As the result, eight data of the photomultipliers 7b to 7i are reduced to four data. The computation processing unit 8 selects the largest data (ΣSa(i)) from among the four luminance sum data in step S65 in the same manner as used in step S65 shown in FIG. 15. Then, the computation processing unit 8 calculates the orthogonal luminance ratio (ΣSa(i)/ΣSb(i)) with referring to the luminance sum data Sb(i) located at the orthogonal position in steps S66 to S67 in the same manner as used in steps 66 and S67. Furthermore, the computation processing unit 8 classifies the defect as the large scratch 23b if the orthogonal luminance ratio (ΣSa(i)/ΣSb(i)) is larger than the set threshold value 50, and on the other hand classifies the defect as the foreign object 24 if the orthogonal luminance ratio is smaller than the set threshold value 50 in step S68. By applying the method described hereinabove, it is possible to discriminate the large scratch 23b, which is apt to be mis-recognized as a foreign object, from the foreign object 24.

Figure 18:
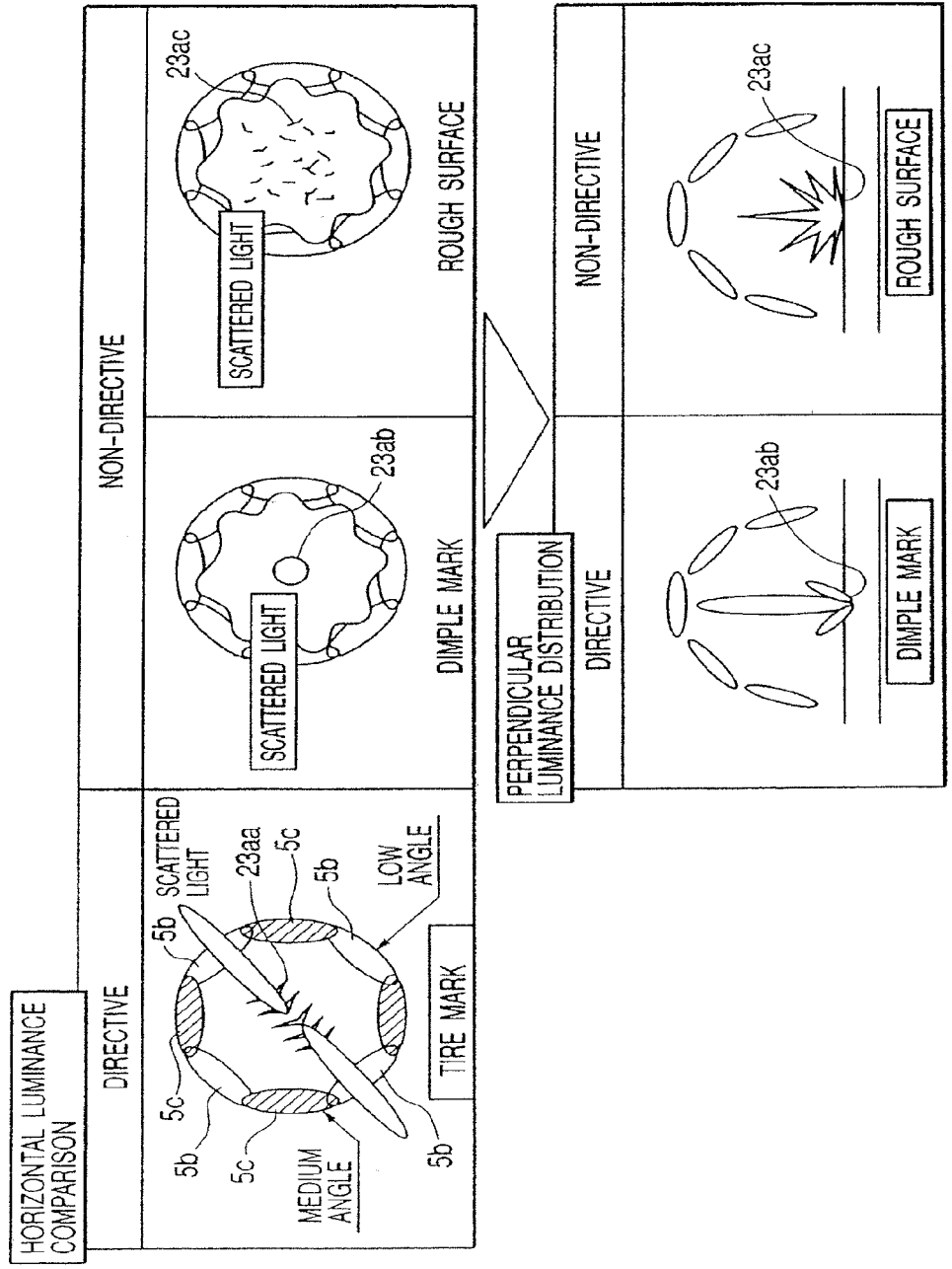
FIG. 18 is a diagram for describing the diffracted light distribution for each scratch configuration in accordance with the present invention.
Figure 19:
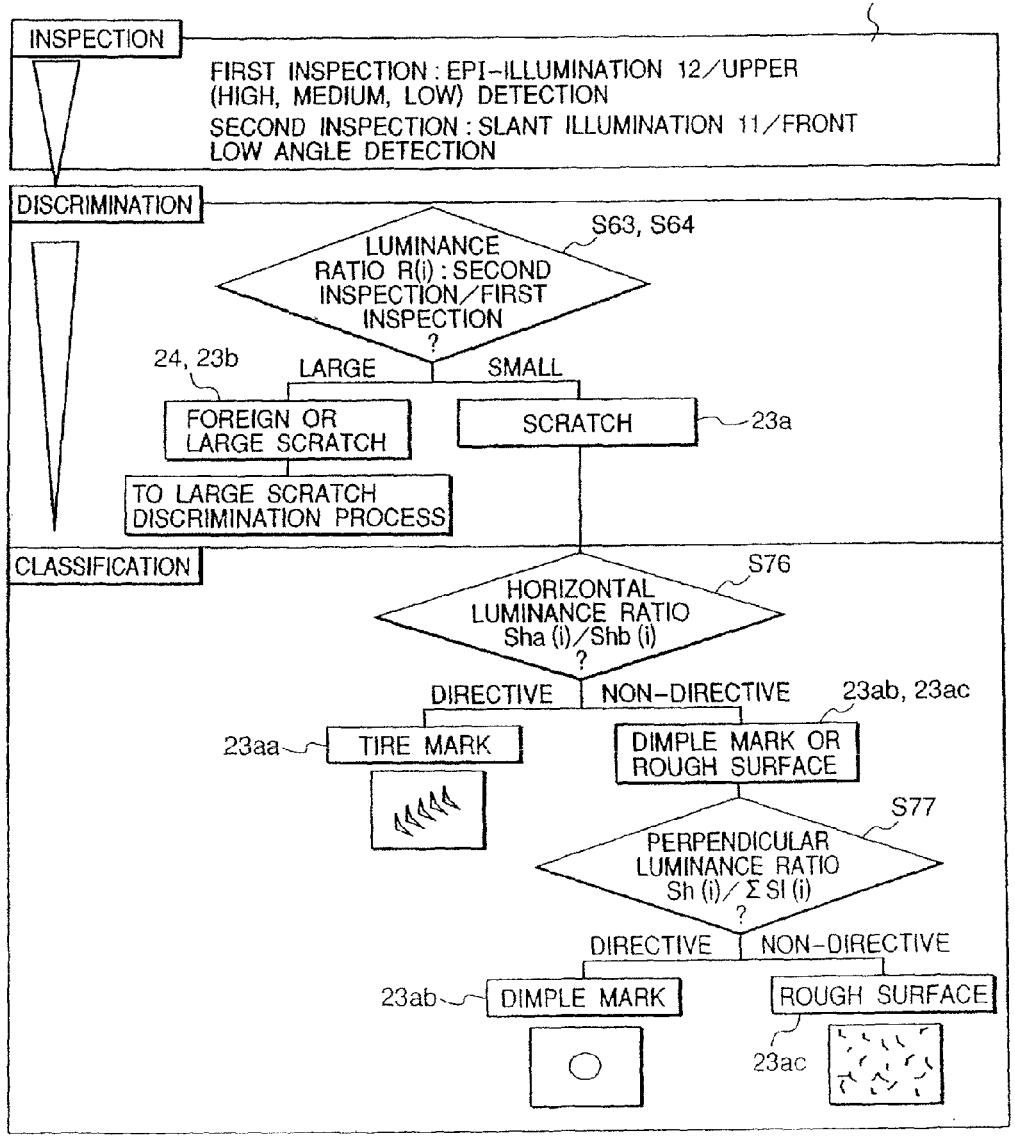
FIG. 19 is a diagram for describing an example of a scratch configuration classification process flow in accordance with the present invention.

Next, the fourth embodiment used to further classify the defect 23a that has been discriminated as the scratch by means of two directional illuminations according to configuration will be described in detail hereinafter with reference to FIG. 18 to FIG. 20B. CMP process involves not only the mechanical polishing but also chemical polishing such as etching simultaneously. Therefore, CMP is called as chemical mechanical polishing. Usually, the mechanical polishing action is predominant in the oxide film polishing process, and a typical scratch 23a is a continuous flaw 23aa comprising small linear scratches, each of which is crescent described as tire mark in FIG. 18. On the other hand, when the chemical polishing action is predominant, the V-shaped flaw 23ab having the circular plane cross section described as dimple mark in FIG. 18 is formed often. Furthermore, when a polishing pad that has been used for long time and has become hard is used, crowded small scratches 23ac that is formed in random direction described as rough surface in FIG. 18 is caused often. As described hereinabove, the configuration of scratch is various depending on the malfunction cause of polishing condition. In other words, by recognizing the scratch configuration with breakdown classification, it is easy to find out the process condition to be improved, and the time required for malfunction countermeasure is significantly shortened. Then, the data discriminated as the scratch 23a in the process for discrimination between the foreign object and the scratch by means of two directional illuminations described hereinabove is classified for configurational breakdown. The scattered light intensity distribution in the horizontal direction and the vertical direction is checked in detail to perform configurational classification of the scratch as shown in FIG. 18. As shown in FIG. 18, because the tire mark 23aa is a linear mark as described in the large scratch discrimination, the tire mark 23aa causes the diffracted light having strong directionality in the horizontal direction. On the other hand, the dimple mark 23ab and the rough surface 23ac do not exhibit the directionality in the horizontal direction scattered light intensity distribution. Then, the dimple mark 23ab is discriminated from the rough surface 23ac by use of the vertical direction scattered light intensity distribution. The discrimination is based on the fact that the dimple mark 23ab exhibits the directionality in the vertical direction but the rough surface does not exhibits the directionality in the vertical direction. To discriminate, the computation processing unit 8 evaluates the diffracted light distribution in the horizontal direction or the vertical direction to thereby classify the defect according to detailed configuration as shown in FIG. 19. The case in which both horizontal and vertical scattered light intensity distributions are used is described in the present example, but the case in which any one of these distributions is used may be employed depending on the configuration to be classified.

In detail, in steps S61 and S62, the first inspection involves the upper detection (high angle detection optical system 5a, medium angle detection optical system 5c, and low angle detection optical system 5b) with the epi-illumination 12, and the second inspection involves the front low angle detection optical system 5b (6b, 7b; 6c, 7c) or high angle detection optical system 5a and/or medium angle detection optical system 5c with slant illumination 11.

Figure 17:
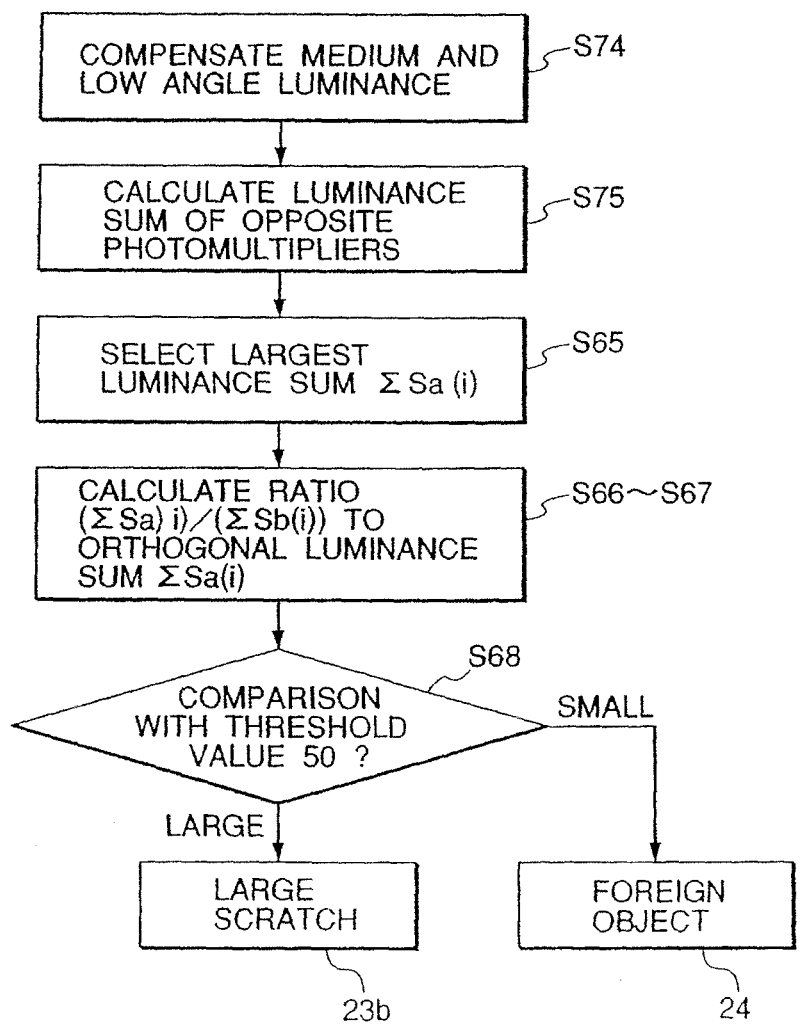
FIG. 17 is a flow chart for describing an example of a discrimination process flow for discriminating between a large scratch and a foreign object in accordance with the present invention.
Figure 20B:
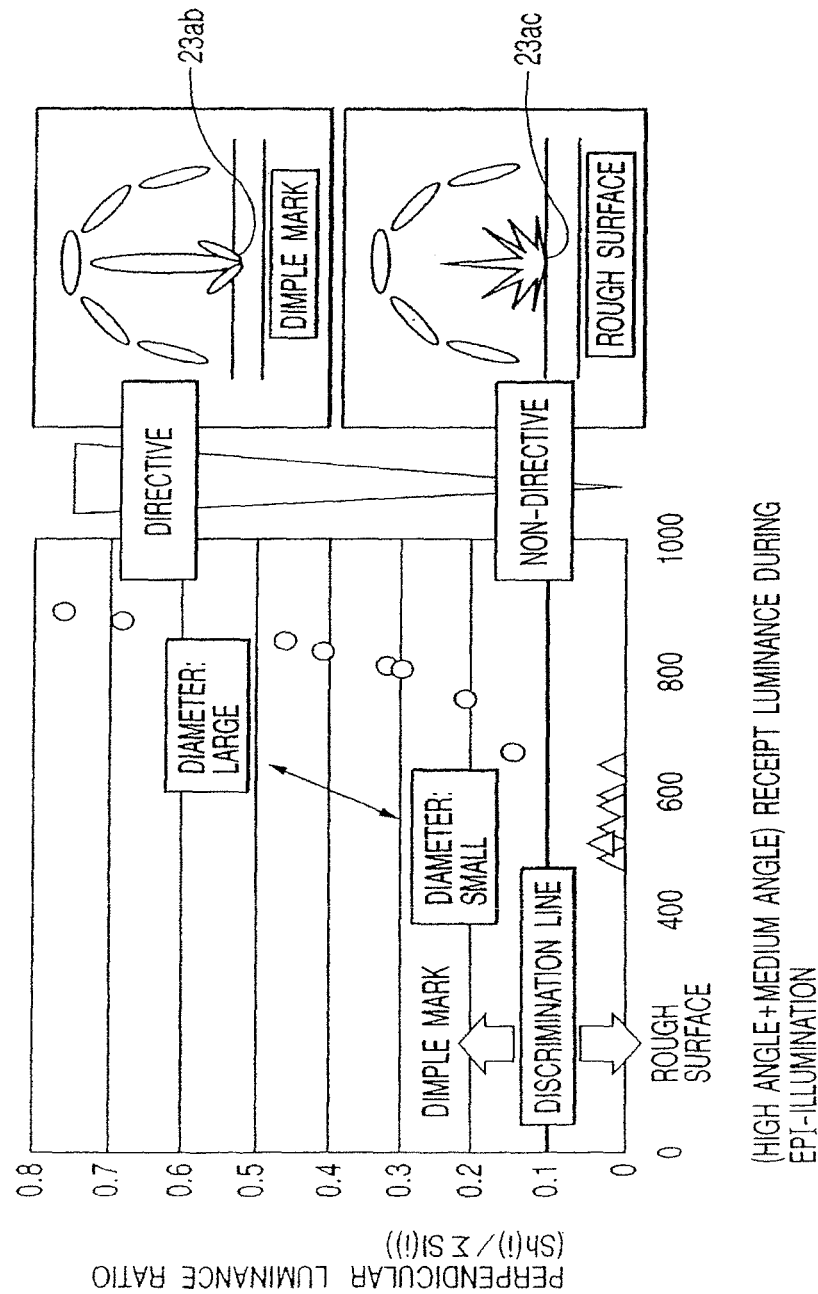

Next, in the present example, the computation processing unit 8 evaluates the horizontal scattered light intensity distribution (Sha(i)/Shb(i)) with the epi-illumination 12 among the data classified as the scratch 23a in steps S63 and S64 in the same manner as used in the method shown in FIG. 17 in step S76 at first, and then classified the data having strong directionality as the tire mark 23aa. Then, the computation processing unit 8 evaluates the vertical directionality in step S77 to thereby classify the defect into the dimple mark 23ab and the rough surface 23ac. In the present example, the horizontal directionality is checked in the same manner as used in the flow shown in FIG. 17. Various methods have been known for evaluation of vertical directionality. For example, the ratio of the detected luminance Sh(i) detected by means of the photoelectric converter 7a of the high angle detection optical system 5a to the sum of the detected luminance ΣSI(i) detected by means of photoelectric converters 7a to 7i of the low angle detection optical system 5b and medium angle detection optical system 5c (Sh(I)/ΣSI(i)) may be calculated. An example of the discrimination result is shown in FIG. 20A and FIG. 20B. FIG. 20A shows the result of evaluation of the horizontal luminance ratio (Sha(i)/Shb(i)) with the epi-illumination 12 to classify into the group of the tire mark 23aa and the dimple mark 23ab or the group of the rough surface 23ac, and the FIG. 20B shows the result of evaluation of the vertical luminance ratio (Sh(i)/ΣSI(i)) with the epi-illumination 12 to classify into the group of the rough surface 23ac and the group of the dimple mark 23ab. In the FIG. 20B, the directionality of the vertical diffracted light of the dimple mark 23ab becomes stronger with increasing of the diameter. This phenomenon agrees with the well-known principle of Airy disk. It is possible to estimate the diameter of a dimple mark based on the luminance ratio.

According to the fourth embodiment described hereinabove, it is possible to discriminatingly inspect the foreign object 24 and the scratch 23 having various configuration on the insulating film flattened by means of CMP process, and the computation processing unit 8 supplies the result to the memory unit 31 connected to the whole control unit 9, and the memory unit 31 stores the result.

Next, the fifth embodiment in accordance with the present invention for previously evaluating whether the defect is classified correctly or not in the above-mentioned surface inspection of the scratch and the like will be described with reference to FIG. 1 and FIG. 21 to FIG. 23. As shown in FIG. 1, the surface inspection apparatus for inspecting the scratch or the like is provided with the memory unit 31, the input means 32 comprising a key board, a mouse, and a memory medium, the display unit 33 comprising a display or the like, and the whole control unit 9 connected to the network 34 connected to, for example, a SEM apparatus. As a matter of course, the memory unit 31 stores the inspection result that has been discriminatingly processed in the computation processing unit 8.

Furthermore, in the surface inspection of the scratch or the like in accordance with the present invention, the sensitivity must be ensured, and also whether the detected defect is classified correctly or not must be evaluated previously. The data must be sampled based on not only the detected luminance information but also discrimination processing result. In detail, it is important that only the doubtful defect that is located near the discrimination line (threshold value) 20 or 50 is selected from among many detected defects and only the selected defect is reviewed by use of a SEM apparatus (not shown in the drawing), that is, only the doubtful defect is subjected to the review selectively for efficient evaluation. As described herein under, the defect of doubtful classification that is located near the discrimination line (threshold value) 20 or 50 displayed on the screen 40 of the display unit 33 is specified. Thereby, the positional coordinate of the defect is acquired. The wafer 10 is placed on a SEM apparatus and the above-mentioned defect is observed by means of SEM based on the acquired positional coordinate, and whether the defect is a foreign object or a scratch 23 of various configuration is evaluated. Then, the review evaluation result obtained by means of the SEM apparatus is supplied to the whole control unit 9 through, for example, the network 34 and stored in the memory unit 31. Thereby, it is possible to review the validity of the discrimination line (threshold value) 20 or 50.

Figure 21:
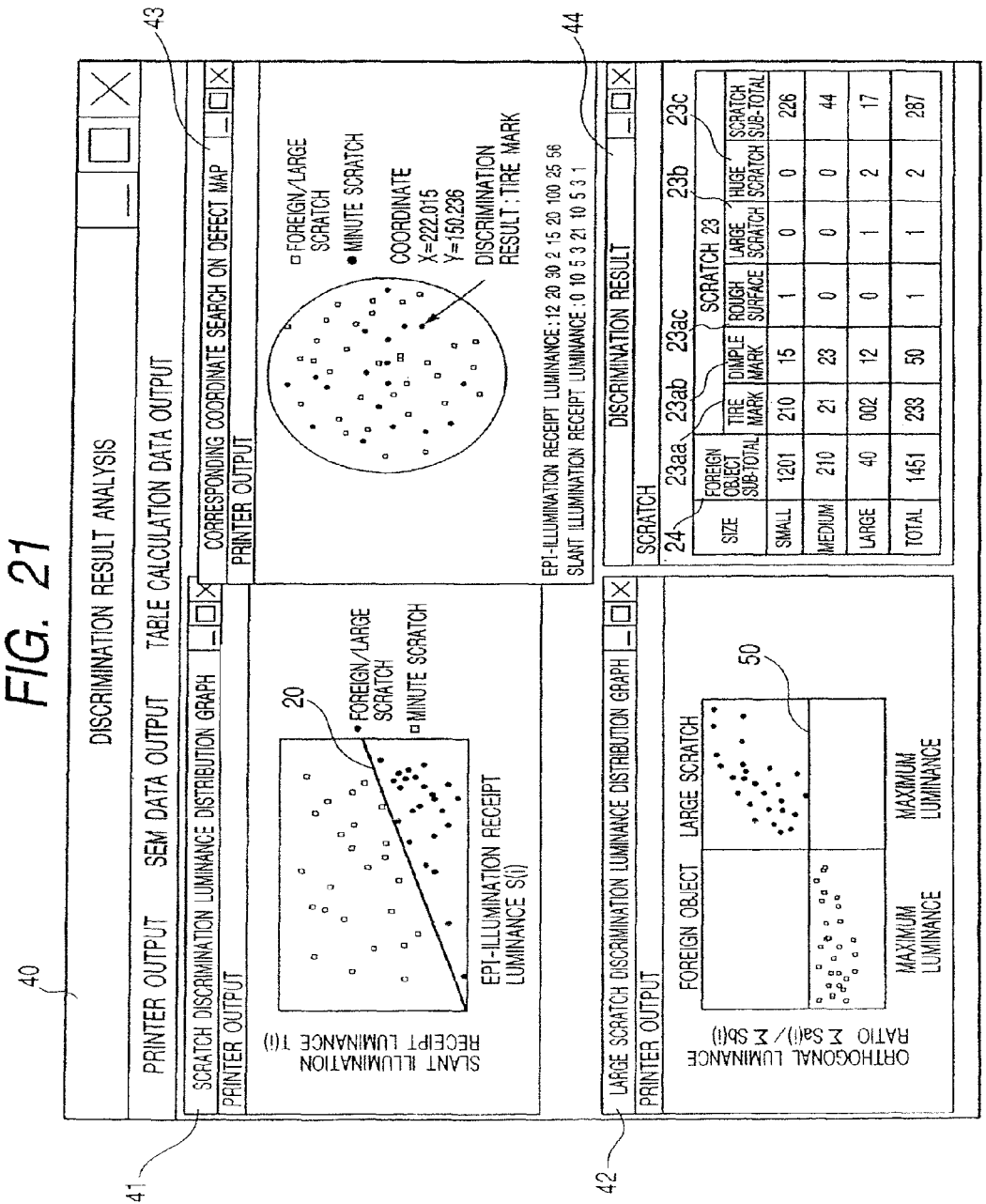
FIG. 21 is a diagram for describing an example of a discrimination result layout displayed on a display unit in accordance with the present invention.

The screen 40 displayed on the display unit 33 is composed of a scratch discrimination luminance distribution graph 41, a large scratch discrimination luminance distribution graph 42, a corresponding coordinate search on defect map 43, and a discrimination result display window 44 as shown in FIG. 21. The scratch discrimination luminance distribution graph 41 shows the relation between the received luminance S(i) with the epi-illumination and the received luminance T(i) with the slant illumination, and shows the state that the defect is discriminated between the small scratch 23a group and the foreign object 24/large scratch 23b group by means of the threshold (discrimination line) 20. The large scratch discrimination luminance distribution graph 42 show the relation between the maximum luminance (ΣSa(i)) and the orthogonal luminance ratio (ΣSa(i)/ΣSb(i)), and shows the state that the defect is discriminated between the foreign object 24 group and the large scratch 23b group by means of the threshold (discrimination line) 50. The corresponding coordinate search on defect map 43 shows the generation state of the scratch 23 and the foreign object 24 on the wafer 10 (defect map). The discrimination result display window 44 shows the number of foreign object 24 and the number of scratches (tire mark 23aa, dimple mark 23ab, rough surface 23ac, large scratch 23b, huge scratch 23c) 23 corresponding to the size (small, medium, and large). The discrimination result display window 44 may be represented in the form of histogram.

The case in which four types of display contents are displayed separately in individual windows is described hereinabove, but the case in which a plurality of graphs are displayed in one window may be employed. Otherwise, the four types of display contents may displayed not simultaneously. The luminance ratio screen that is obtained by analyzing the scratch content by use of the horizontal and vertical luminance ratios may be displayed by selecting it on the pull down menu though it is not shown in the drawing. It may be possible to display the defect coordinate, discrimination result, and the received luminance of each of the photoelectric converters 7a to 7i in one or a plurality of items by pointing the defect on the defect map with a cursor or the like in the corresponding coordinate search on defect map 43. Furthermore, on the one of the scratch discrimination luminance distribution graph 41 and the large scratch discrimination luminance distribution graph 42, or on both the graphs, it may be possible that the data corresponding to the defect pointed by use of a cursor or the like is blinked, color of the data is changed, or the size of the display mark is changed so that an operator can easily recognize the corresponding data. Furthermore, it may be possible that, when the data point is selected by use of an input means 32 such as a cursor or the like on the scratch discrimination luminance distribution graph 41 or the large scratch discrimination luminance distribution graph 42, the display mark is blinked, the color is changed, or the size of the display mark is changed on the defect map so that an operator can easily discriminate the corresponding data from other data on the monitor 33. Furthermore, one or a plurality of information of the defect coordinate, discrimination result, and received luminance of each of the photoelectric converters 7a to 7i of the data specified on the graphs 41 and 42 may be displayed. As described hereinabove, an arbitrary defect data is selected on the graph 41 or 42 or the defect map 43 and the specified inspection information is displayed on the monitor 33. Thereby, it is possible to complete the examination of the validity of the discrimination processing within a short time.

As described hereinabove, it is possible to display the inspection result stored in the memory unit 31 (the coordinate data of the foreign object 24 and the scratch 23, discrimination result of the foreign object 24 and various scratch 23, and received luminance data obtained from the photoelectric converters 7a to 7i with the epi-illumination and the slant illumination) on the screen of the display unit 33, and it is possible to review whether the detected defect is classified correctly or not. Particularly, it is possible to review the validity of the discrimination line (threshold value) 20 or 50 served for discrimination on the graph displays 41 and 42.

Furthermore, as shown in FIG. 21, the size of the defect of each classification of the foreign object 24 and the scratch 23 is estimated correspondingly to the magnitude of the received luminance obtained from the photoelectric converters 7a to 7i as shown in the discrimination result 44, the defect is classified into some categories, and the frequency of the defect is displayed category-wise. This method is effective for efficient use of the inspection result. The foreign object 24 and scratch 23 that is sufficiently smaller than the design value of the semiconductor such as wiring interval (the size is very small) seldom affect the function of the product fatally. On the other hand, when many very large defects occurs (having large size), the production must be shutdown immediately. In other words, the countermeasure is different depending on the size of the detected defect. Then, as shown in the discrimination result 44, the defect is categorized into three categories, namely small size defect, medium size defect and large size defect. The small size defect is the very small defect that is not fatal, the medium size defect is the defect that is apt to result in fatal result, and the large size defect is the defect that results in fatal result inevitably. The number of categories is by no means limited to three, but may be one or a plurality of categories arbitrarily depending on the application. Three categories are set for all the classifications of the foreign object 24 and the scratch 23, but the different number of categories may be set for each classification of the foreign object or scratch. The subtotal may be calculated for each category. The total may be calculated for the foreign object 24 and the scratch 23 respectively. The total number of defects of the foreign object 24 and the scratch 23 may be displayed.

As described hereinabove, the whole control unit 9 is structured so as to generate the subtotal for the foreign object 24 category and various scratch 23 category or the total as the discrimination result 44. Thereby, it is possible to manage the subtotal for these categories and the total number when the present invention is introduced to the manufacturing process, and as the result it is possible to monitor the occurrence of the scratch 23 and foreign object 24 efficiently, and the suitable countermeasure can be applied.

Figures 22, 23:
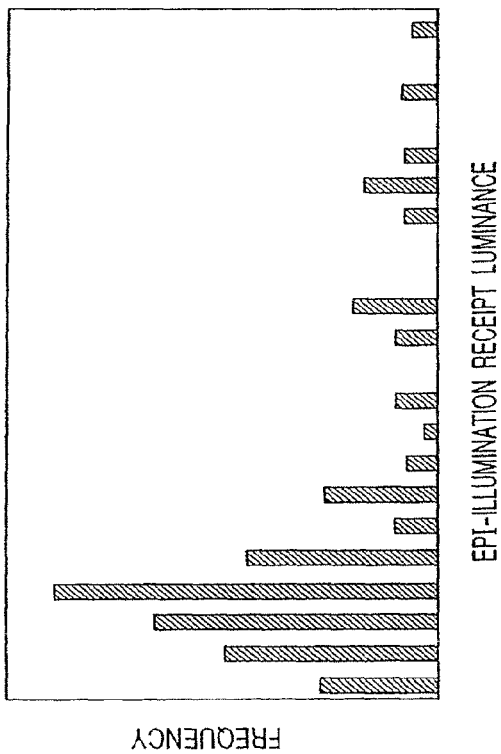
FIG. 22 is a graph for describing an example of a tire mark luminance distribution in accordance with the present invention.
FIG. 23 is a diagram for describing an example of table calculation data items in accordance with the present invention.

Furthermore, the whole control unit 9 is provided with a frequency distribution display function to show the defect size distribution in detail. As shown in FIG. 22, the abscissa represents the received luminance when the epi-illumination is irradiated and the ordinate represents the frequency. In FIG. 22, the frequency distribution is displayed only for the defect data that is classified as the tire mark 23aa. The frequency distribution may be displayed for the defect data that is classified as each classification of the foreign object 24 and the scratch 23, or for all the defect data that is recognized as the scratch, or for all the defect data including the foreign object 24 and the scratch 23. Any of various combinations may be displayed. Though not shown in the drawing, any of various combinations can be selected by means of the pull down menu. The abscissa may represent the luminance of each of photoelectric converters 7a to 7i, or may represent the received luminance sum of the photoelectric converters 7a to 7i for arbitrary combination of these photoelectric converters 7a to 7i. Furthermore, the same processing may be performed for the slant illumination data. By using the frequency distribution display function, not only the defect distribution can be analyzed in detail but also the scattered light distribution can be analyzed easily in detail.

Furthermore, the exclusive analysis tool is effectively used to analyze the inspection data, and also the commercially available spreadsheet software that is used for various calculation may be easily used effectively to shorten the evaluation time. Then, the entire inspection data or selected partial inspection data is saved for the items shown in FIG. 23 in the memory unit 31 such as hard disk or floppy disk in the format that is readable by use of the spreadsheet software. In the present example, the identification number given to the defect, discrimination result, received luminance obtained by means of each of the photomultipliers 7a to 7i when the epi-illumination is irradiated, and the received luminance obtained by means of each of the photomultipliers 71 to 7i when the slant illumination is irradiated are written in the memory unit 31. Not all these data are necessary. In some cases, it is meaningful to save the defect coordinate data. By reading the data by use of the commercially available spreadsheet software, the whole control unit 9 is made possible to analyze the data of the detected defect easily, and the discrimination capability is improved within a short time.

The method in which a plurality of photoelectric conversion means 7a to 7i is used to evaluate the three-dimensional intensity distribution of the diffracted light is described hereinabove.

Next, the third example of a surface inspection apparatus for inspecting the scratch or the like served to obtain the two-dimensional distribution of the diffracted light easily will be described with reference to FIG. 24 to FIG. 26B. The present example shows an apparatus that is formed by adding a detection optical system comprising lenses 108 and 106, CCD cameras 104 and 107 and a beam splitter 105 to the high angle detection optical system 5a in the example shown in FIG. 1 or FIG. 9. Therefore, also in the present example, there are the epi-illumination system and the slant illumination system, and the defect is discriminated between the foreign object 24 and the small scratch 23a based on the luminance ratio. The two-dimensional photoelectric conversion means such as TDI sensor may be used as the added CCD cameras 104 and 107. Furthermore, though two CCD cameras 104 and 107 are used in the present example, the structure in which one CCD camera is moved to two positions, namely the image forming plane and the Fourier transformation plane, may be employed. The one CCD camera 104 is located so that the image forming plane of the camera is coincident with the image forming plane of the lens 108. The other CCD camera 107 is located so that the image forming plane of the camera is coincident with the Fourier transformation plane of the lens 106.

At first, in the computing unit 18a of the computation processing unit 8, by use of the image forming data, which is obtained by means of the CCD camera 104, ND converted by means of the A/D conversion unit 16a, and stored in the memory unit 17a, for example, the signal that is converted to the binary signal with a desired threshold value for indicating the defect is extracted to thereby search the position of the defects 23 and 24, and the searched result is supplied to and stored in the memory unit 31 as the positional coordinate of the defects. The whole control unit 9 controllably drives the stage 15 according to the control command supplied from the stage controller 14 based on the positional coordinate of the searched defects, and positions the defects 23 and 24 at the visual field center of the CCD camera 107.

Figure 25A:
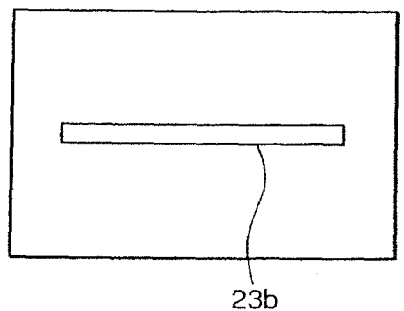
FIG. 25A and FIG. 25B are diagrams illustrating an example of the diffracted light distribution on the Fourier transformation plane shown in FIG. 24.
Figure 25B:
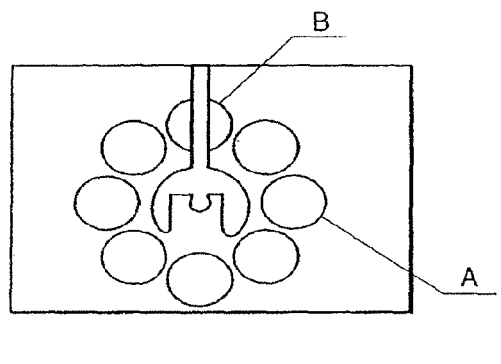
Figure 26:
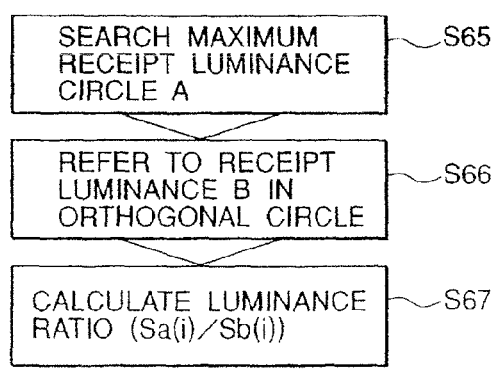
FIG. 26 is a flow chart for describing an example of a diffracted light distribution evaluation flow on the Fourier transformation plane shown in FIG. 24.

Next, the computing unit 18b of the computation processing unit 8 performs the evaluation as described herein under by use of the image data that is obtained by means of the CCD camera 107, ND-converted by means of the ND conversion unit 16a, and stored in the memory unit 17a. For example, in the case that there is a linear defect like the large scratch 23b in the horizontal direction as shown in FIG. 25A, the diffracted light is distributed in the vertical direction in FIG. 25B on the Fourier transformation plane. It becomes possible that the horizontal diffracted light distribution is evaluated by evaluating by use of the algorithm shown in FIG. 26. At first, in the computing unit 18b, eight luminance evaluation regions that are indicated with circles in FIG. 25B are set around the point where zero order diffracted light is received as shown in FIG. 25A. The luminance evaluation region is a circle in the present example, but the region is not necessarily circular. The region may be quadrangular or polygonal. Furthermore, eight luminance evaluation regions are set in the present example, but the number of regions may be more or less depending on the accuracy for evaluation of the scattered light intensity distribution. The number and the configuration of the region are by no means limited. Then, the computing unit 18b calculates the received light sum (Si) of each pixel in each set luminance evaluation region. The horizontal diffracted light directionality is evaluated according to the process flow S65, S66, and S67 shown in FIG. 26 by use of eight luminance sums in the same manner as used in the method shown in FIG. 15 or FIG. 17. The light of the light source 2 is irradiated from the direction near the normal line of the wafer 10 in the present example, but the light may be irradiated from the slant direction. The diffracted light in the normal line direction of the wafer 10 is received in the present example, but the diffracted light in the slant direction may be received. The pseudo perpendicular illumination obtained by locating the reflection mirror 4c at the position outside the NA of the lens 108 so that the regular reflected light reflected from the wafer 10 is not received is used in the present example, but the perpendicular illumination may be used.

Figure 27:
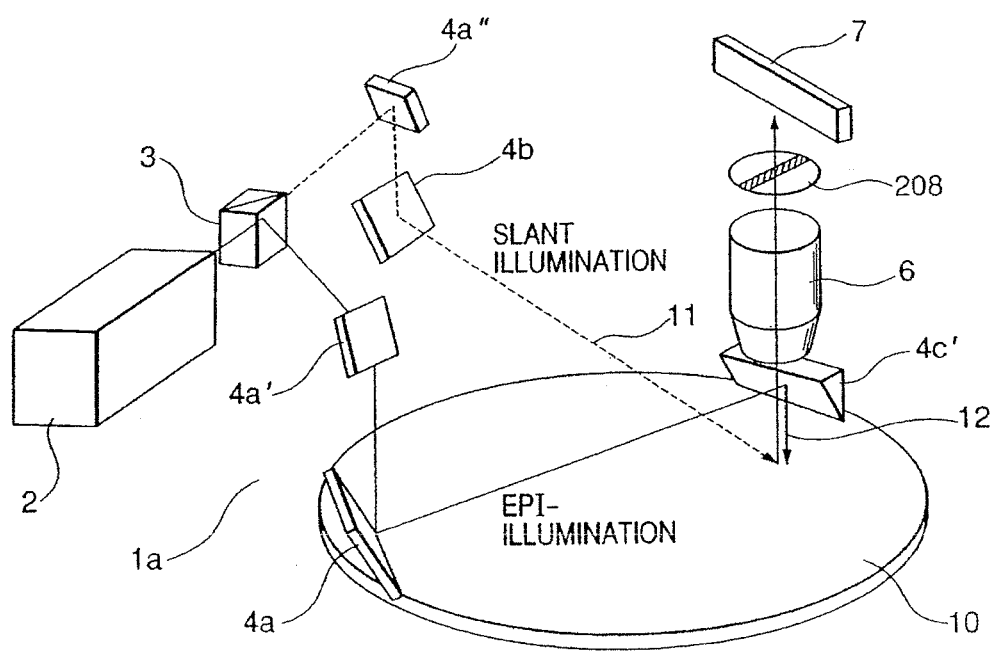
FIG. 27 is a perspective view illustrating an example in which an example of a surface inspection apparatus in accordance with the present invention is applied to a wafer having a wiring pattern.
Figure 28:
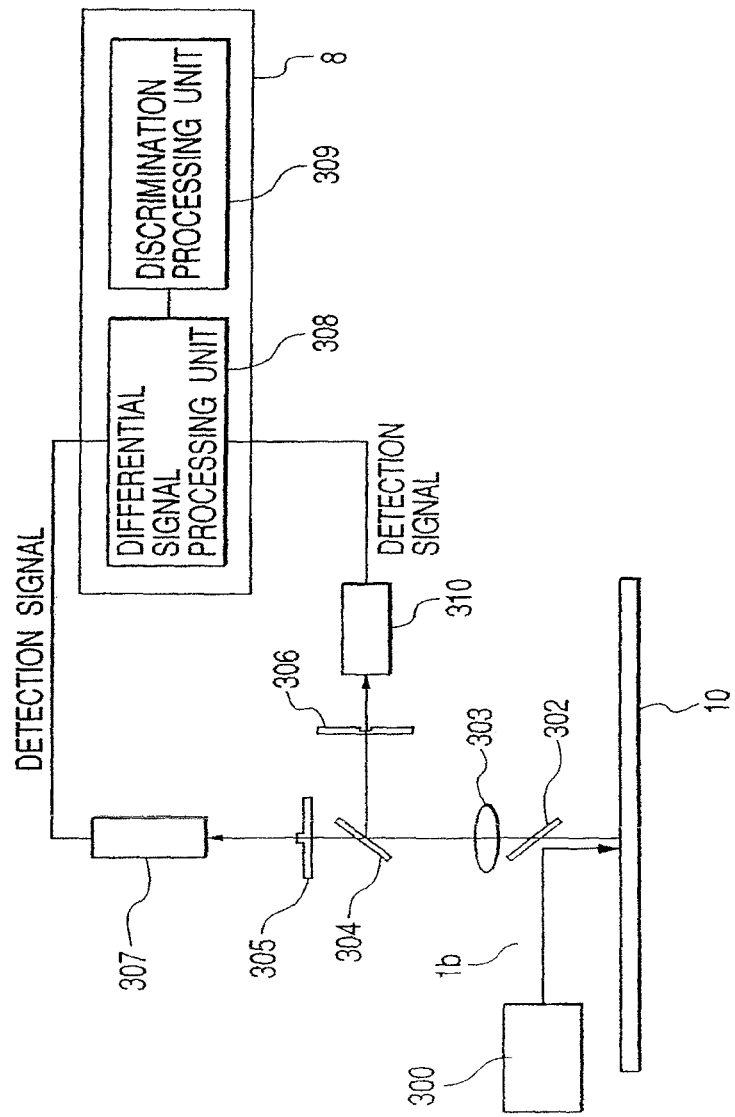
FIG. 28 is a schematic structural diagram illustrating the fourth example of a surface inspection apparatus in accordance with the present invention.

The case in which the method is applied to a wafer 10 having no wiring pattern is mainly described hereinbefore. When this method is applied to a wafer 10 having wiring pattern, a space filter 208 is provided as shown in FIG. 27. However, in some cases, the space filter is not necessarily required depending on the case. In the present example, the case in which it is required to remove the diffraction pattern based on the diffracted light emitted from the periodical wiring pattern by use of, for example, a linear space filter as described in Japanese Unexamined Patent Publication No. H6-258239 will be described. The structure of the present example will be described with reference to FIG. 27. The present example is provided with a wafer 10 that is an object to be inspected, an illumination unit comprising a light source 2, an optical path switching mechanism 3, reflection mirrors 4a'', 4b, 4a', 4a, and 4c', and a detection unit comprising a lens 6, a space filter 208, and photoelectric conversion means 7. In the present example, one light source 2 is switched between the epi-illumination 12 and the slant illumination 11 by use of the optical path switching mechanism 3 and the reflection mirrors 4a'', 4b, 4a', and 4a, but the number of light sources and the number of reflection mirrors are by no means limited. The number of light sources may be smaller or larger than two. The same discrimination principle and discrimination processing method as applied to the above-mentioned examples are applied also to the present example. The any one of perpendicular illumination and pseudo perpendicular illumination shown in FIG. 7A to FIG. 7D may be used as the epi-illumination.

The defect is discriminated between the scratch 23 and the foreign object 24 by analyzing the distribution and the intensity of the scattered light emitted from the scratch 23 based on the specific configuration of the scratch by use of the computation processing unit 8 in the method described hereinbefore. Furthermore, the configuration of the scratch 23 is classified in detail.

Next, the fourth example of a surface inspection apparatus for inspecting the scratch or the like served to realize the first embodiment in accordance with the present invention will be described with reference to FIG. 28 to FIG. 34. In detail, in the fourth example, the defect is discriminated between the concave and the convex based on the fact that the foreign object 24 is convex and the scratch 23 is concave inherently. To say to avoid the misunderstanding again, the above-mentioned discrimination method between the foreign object 24 and the scratch 23 does not involve the discrimination between the convex and the concave, but involves discrimination based on the difference in aspect ratio between the width W and the depth D or height of the scratch 23 and the foreign object 24.

The fourth example is provided with an illumination optical system comprising a light source 300 and a half mirror 302 for illuminating from the perpendicular direction of the wafer 10, a detection optical system comprising a behind phase filter 305 located on the Fourier transformation plane, an ahead phase filter 306, a beam splitter 304 for splitting the light that passes through the filters 305 and 306, and photoelectric conversion means 307 and 310, and a computation processing unit 8 comprising a differential signal processing unit 308 for making the difference between detected luminance obtained from the photoelectric conversion means 307 and 310 and a discrimination processing unit 309 for recognizing the convex and the concave based on the differential signal. In the fourth example, the photomultiplier A310 and the photomultiplier B307 are used as the photoelectric conversion means. At first, the behind phase filter 305 and the ahead phase filter 306 are described with reference to FIGS. 29A and 29B and FIG. 30. The behind phase filter 305 delays the phase of the light that passes near the region with respect to the periphery where the zero order diffracted light passes. In detail, an optically flat plate having a thickness of t with additional thickness d on the region where the zero order diffracted light passes is used. The optical path length L on the periphery and the optical path length L' on the region where the zero order diffracted light passes are calculated according to the equation 2 and the equation 3 respectively, wherein n denotes the refractive index of the plate and $n_0$ denotes the refractive index of air.

$$L = n \times t + n_0 \times d \quad \text{(equation 2)}$$

$$L' = n \times (t+d) \quad \text{(equation 3)}$$

In other words, the optical path length of the light that passes the periphery and the optical path length of the light that passes the region where the zero order diffracted light passes make the optical path difference $\Delta L1$ represented by the following equation 4.

$$\Delta L1 = L' - L = (n - n_0) \times d \quad \text{(equation 4)}$$

The refractive index of the air is assumed to be 1 and the refractive index is approximately 1.5 when glass material is used for the plate. Therefore, the optical path length difference $\Delta L$ is represented by the following equation 5 in detail.

$$\Delta L1 = (1.5 - 1) \times d = 0.5 \times d \quad \text{(equation 5)}$$

On the other hand, the ahead phase filter 306 has a thin thickness of (t−d) on the region where the zero order diffracted light passes as shown in FIG. 30. Such structure makes the optical path length difference $\Delta L2$ as represented by the equation 6 in the same manner as described hereinabove.

$$\Delta L2 = (n_0 - n) \times d \quad \text{(equation 6)}$$

In the above-mentioned detailed case, the optical path length $\Delta L2$ is represented by the equation 7 in detail.

$$\Delta L2 = -0.5 \times d \quad \text{(equation 7)}$$

In the case of the light source having a wavelength of $\lambda$, the light that has passed the region of the zero order diffracted light has the behind phase of $\theta 1$ (rad.) and the ahead phase of $\theta 2$ (rad.) with respect to the peripheral passing light as represented by the equation 8 and the equation 9.

$$\theta 1 = \Delta L1 / \lambda \times 2\pi = (n - n_0) \times d / \lambda \times 2\pi \quad \text{(equation 8)}$$

$$\theta 2 = \Delta L2 / \lambda \times 2\pi = (n - n_0) \times d / \lambda \times 2\pi \quad \text{(equation 9)}$$

In the case that a light source for emitting the light having a wavelength $\lambda = 488$ nm is used, the phase deviation is equal to the detailed value represented by the following equation 10 and equation 11 in the above-mentioned detailed example.

$$\theta 1 = 0.5 \times d / 488 \times 2\pi \quad \text{(equation 10)}$$

$$\theta 2 = -0.5 \times d / 488 \times 27\pi \quad \text{(equation 11)}$$

To make the behind phase θ1 and the ahead phase θ2 to be the phase deviation of θ1=π/2 and θ2=−π/2 respectively, d may be the value represented by the following equation 12 and equation 13.

$$\theta1=\pi/2=0.5\times d/488\times 2\pi$$

Therefore, d=244 nm (equation 12)

$$\theta2=-\pi/2=-0.5\times d/488\times 2\pi$$

Therefore, d=244 nm (equation 13)

As described hereinabove, the discrimination principle for discriminating between the scratch 23 and the foreign object 24, that will be described herein under, can be realized by use of the phase filters 305 and 306 designed as described hereinabove.

Figure 31:
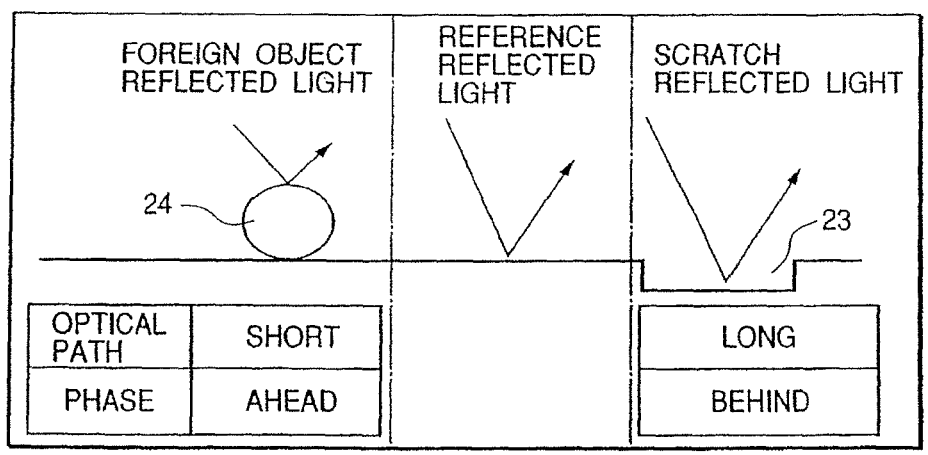
FIG. 31 is an explanatory diagram for describing the phase difference caused by a scratch and foreign object in accordance with the present invention.

The discrimination principle for discriminating between the foreign object 24 and the scratch 23 will be described with reference to FIG. 31. The laser irradiated onto the wafer 10 is a plane wave having the same phase. The light regularly reflected from the wafer surface having no defect is also a plane wave having the same phase. The regular reflected light is referred to as reference reflected light. The optical path length of the light reflected from the foreign object 24, namely the convex, is shorter than that of the reference reflected light. Therefore the phase of the reflected light emitted from the convex is ahead with respect to the phase of the reference reflected light. On the other hand, the optical path length of the reflected light from the scratch 23, namely the concave, is longer than that of the reference reflected light by the indent, and the phase is behind. In other words, when a light flux 12 is irradiated on the surface having the convex and concave, the phase of the light reflected from the concave and the convex is behind for the concave and ahead for the convex respectively with respect to the phase of the laser reflected from the flat portion. Then, in the present invention, two types of phase filters 305 and 306 are inserted on the Fourier transformation plane, the differential signal processing unit 308 detects the ahead phase and the behind phase due to the concave and the convex respectively, and the discrimination processing unit 309 discriminate the defect based on the detected ahead and behind phase. Thereby, the defect is discriminated between the foreign object 24 and the scratch 23. The data obtained as described hereinabove is stored in the memory unit 31 connected to the whole control unit 9 together with the positional coordinate data.

Furthermore, the details are described with reference to FIG. 32 to FIG. 34.

At first, the differential signal intensity served for detecting the scratch 23, namely the concave, by means of the differential signal processing unit 308 and the discrimination processing unit 309 of the computation processing unit 8 will be described in detail herein under with reference to FIG. 32. In the phase vector diagram, the clockwise direction represents the behind phase and the anticlockwise direction represents the ahead phase with respect to the reference phase of the reference reflected light having the phase that has not been changed. The photomultiplier A310 receives the light that has passes through the ahead phase filter 306. On the other hand, the photomultiplier B307 receives the light that has passes through the behind phase filter 305. The regular reflected light component coming from the wafer surface is converged at the point on the Fourier transformation plane and passes through the phase change region formed at the center of the phase filter. As the result, the phase of the reference light that has passed through the ahead phase filter 306 becomes the vector 321 that is ahead 90 degrees anticlockwise on the phase vector diagram. On the other hand, the scattered light emitted from the scratch 23 becomes the approximately parallel light at the Fourier transformation plane and passes through the peripheral region of the phase filters 306 and 305.

Figure 32:
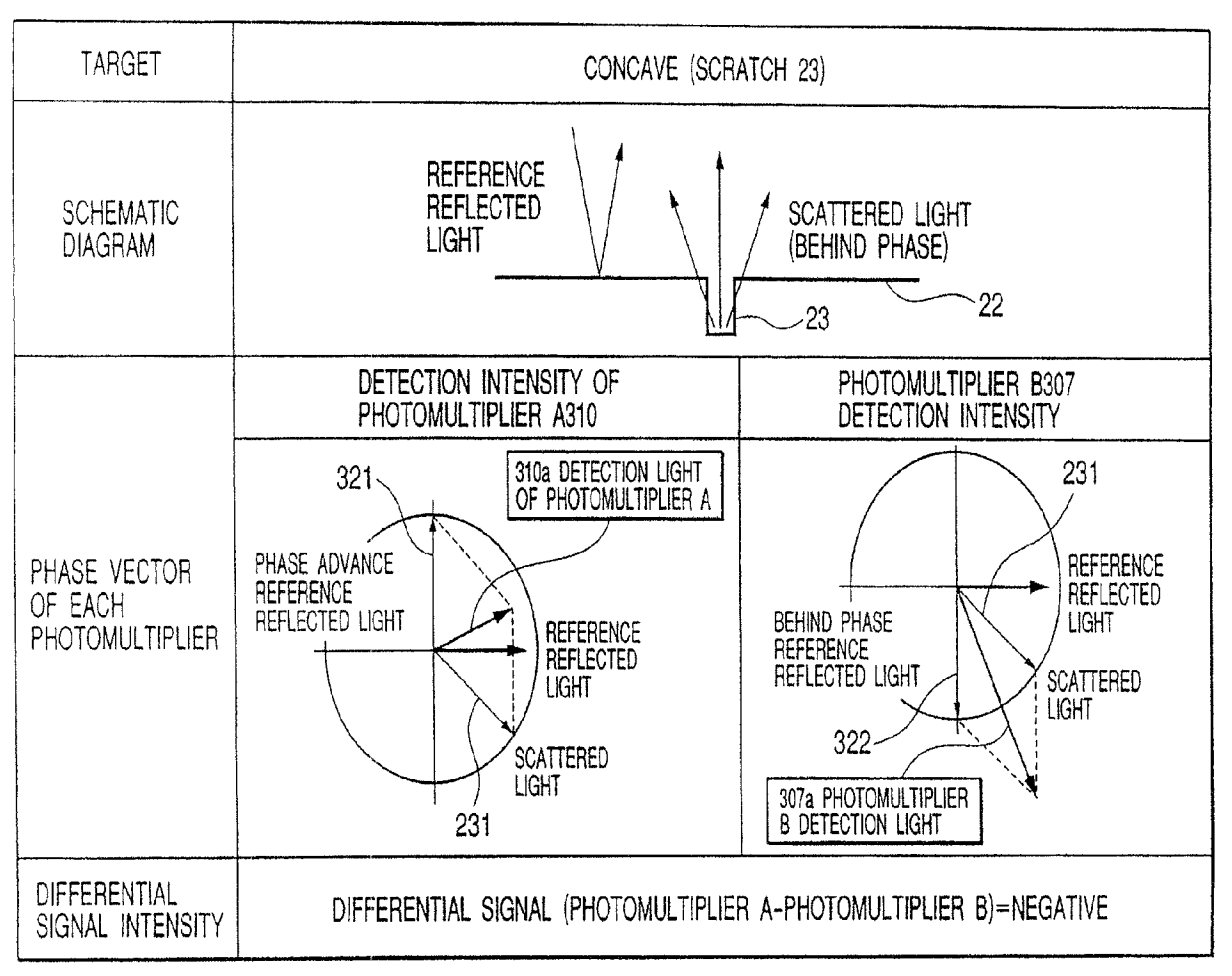

Therefore, the scattered light emitted from the scratch 23 having the behind phase with respect to that of the reference transmitted light becomes the vector that deviates clockwise as shown on the left side of the phase vector diagram shown in FIG. 32. An image is formed by means of interference between the reference reflected light 321 having the ahead phase and the scattered light 231 having the behind phase on the image forming plane. It is the sum of the reference light vector 321 having the phase that has been made 90 degrees ahead by means of the phase filter 306 and the scattered light vector 231 having the phase that has been made behind by means of the concave on the phase vector diagram, and represents the image forming vector that arises from the interference of the photomultiplier A detected light vector 310a shown in FIG. 32. In other words, the luminance of the formed image is represented by the length of the photomultiplier A detected light vector 310a.

Similarly, the luminance of the formed image that has passes through the behind phase filter 305 is represented by the phase vector of the sum of the reference light vector 322 having the phase that has been made 90 degrees behind by means of the phase filter 305 and the scattered light vector 231 having the phase that has been made behind by means of the concave, namely the photomultiplier B detected light vector 307a on the right side. The photomultiplier B detected light vector 307a is larger than the photomultiplier A detected light vector 310a. That is, the magnitude of the synthetic vector formed by deviating the phase of the reference light in the same direction as that of the phase deviation of the scattered light detected by means of the photomultiplier B307 is larger.

Therefore, the differential signal processing unit 308 of the computation processing unit 8 subtracts the photomultiplier B detected luminance 307a from the photomultiplier A detected luminance 310a to give a negative differential signal. Based on the negative differential signal, the discrimination processing unit 309 discriminates the defect as the scratch 23, namely the concave.

In FIG. 34, an example of a dark field image in which, a two-dimensional photoelectric conversion means, for example, a CCD camera is used as the photoelectric conversion means 310 and 307 is used is shown. Each luminance distribution shows the luminance profile on the a-a' cross section and b-b' cross section on the image data. The left side diagram of FIG. 34 shows the case of the scratch 23. The dark field image that has passed through the ahead phase filter 306 is darker than the dark field image that has passed through the behind phase filter 305. As described hereinabove, in the case that the two-dimensional photoelectric conversion means is used, the differential signal processing unit 308 of the computation processing unit 8 may calculate the difference of the maximum value in the detected luminance profile.

Next, the differential signal intensity for detecting the foreign object 24, namely the convex, by means of the differential signal processing unit 308 and the discrimination processing unit 309 of the computation processing unit 8 will be described in detail with reference to FIG. 33. The phase of the scattered light 241 is made ahead with respect to the phase of the reference light in the case of the foreign object 24, namely the concave. Therefore, the intensity on the image forming plane of the received light 310b that has passed through the ahead phase filter 306 received by mean of the photomultiplier A310 is stronger than the intensity of the received light 307b that has passed through the behind phase filter 305 received by means of the photomultiplier B307. As the result, the differential signal processing unit 308 gives the positive differential signal. Based on the positive differential signal, the discrimination processing unit 309 discriminates the defect as the foreign object 24, namely the convex.

Furthermore, as shown on the right side of FIG. 34, in the case of the foreign object 24, the dark field image that has passed through the ahead phase filter 306 is brighter. As described hereinabove, in the case that the two-dimensional photoelectric conversion means is used, the differential signal processing unit 308 of the computation processing unit 8 may calculate the difference of the maximum value in the detected luminance profile.

As described hereinabove, the differential signal of the luminance signal obtained from the differential signal processing unit 308 changes between negative and positive depending on the concave and convex configuration of the defect including the scratch 23 and the foreign object 24. Therefore, the discrimination processing unit 309 checks whether the signal is negative or positive to thereby discriminate whether the defect is a scratch 23 or a foreign object 24. Furthermore, it is possible that the discrimination processing unit 309 converts the differential signal intensity to the depth or height information easily.

Only the case in which the scratch 23 is included as the defect type is described in the fourth embodiment described hereinabove. The configuration is classified by means of the directionality of the diffracted light only in the case of the defect that has been previously classified as the scratch 23 or only in the case of the defect that has been previously classified as the foreign object 24 in the front half of the first to fourth embodiments. However, as a matter of course, the computation processing unit 8 can easily realize the configuration classification of the defect by use of the classification function based on the directionality for the defect including only the foreign object 24 and for the defect including only the scratch 23. Furthermore, it is possible to combine the convex/concave discrimination method based on the phase difference described in the rear half of the first to fourth embodiments and the diffracted light distribution evaluation method described in the front half of the first to fourth embodiments.

According to the invention described hereinabove, ADC (Automatic Defect Classification) or on-the-fly ADC in which the type of the defect is classified synchronously or asynchronously with the defect detection while the defect is being detected is realized.

Next, an embodiment for inspecting the defect located near the wafer edge will be described with reference to FIG. 35 to FIG. 40.

Figure 10:
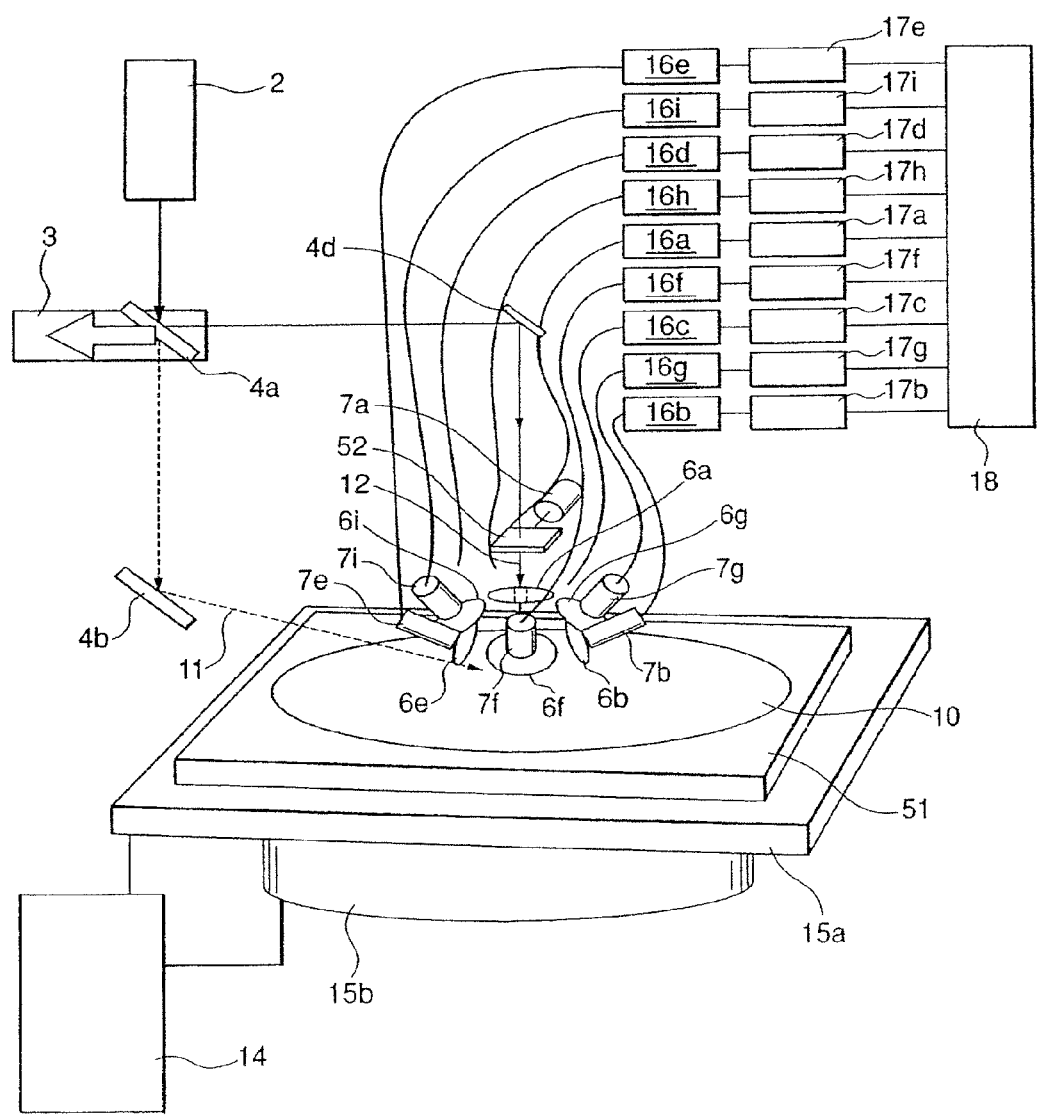
FIG. 10 is a schematic structural diagram for illustrating the second example in which a surface inspection apparatus involves multiple direction light receiving in accordance with the present invention.
Figure 35:
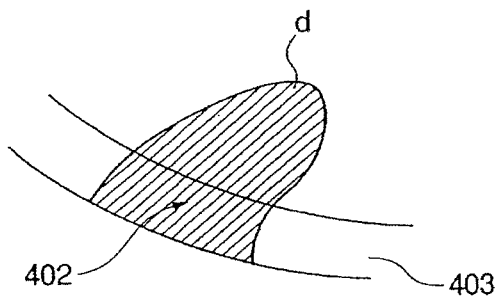
FIG. 35 is an enlarged perspective view illustrating a wafer edge portion.
Figure 36:
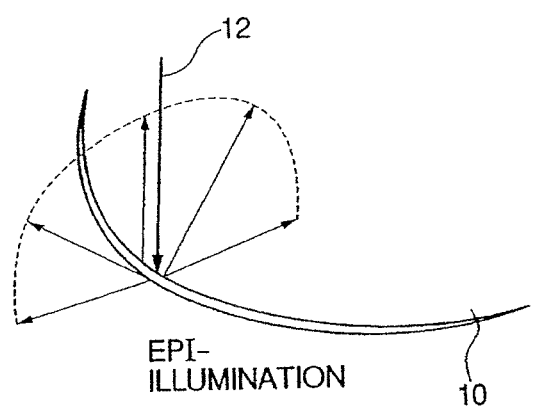
FIG. 36 is a perspective view illustrating the scattered light distribution scattered from the wafer edge portion when epi-illumination is irradiated.
Figure 37:
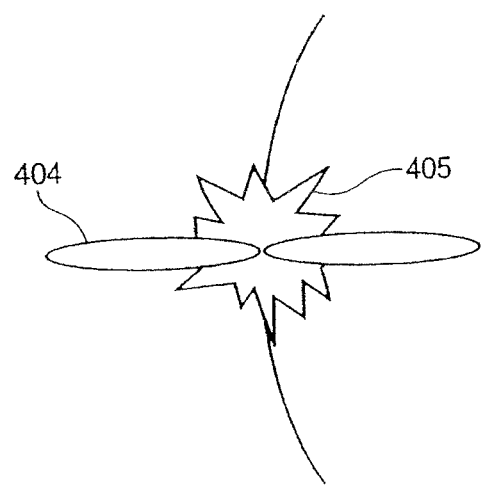
FIG. 37 is a plan view illustrating the scattered light distribution scattered from a wafer edge portion and defect when epi-illumination is irradiated.
Figure 38:
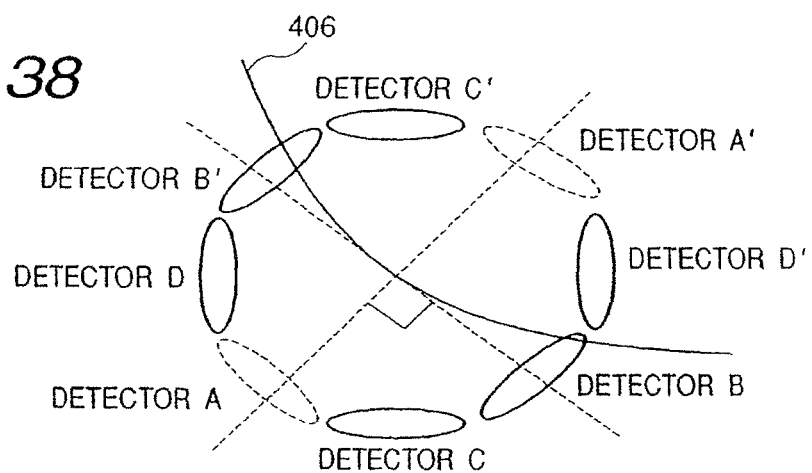
FIG. 38 is an explanatory diagram illustrating an example for discrimination processing between a wafer edge portion and defect.

At first, the case in which the present embodiment is applied to the converging detection optical system shown in FIG. 10, FIG. 11A, and FIG. 11B. In detail, FIG. 35 shows the case in which a defect 402 such as a scratch 23 or a foreign object 24 adheres near the wafer edge 403. In this case, when the illumination light 11 or 12 such as a laser is irradiated onto the defect 402 such as the scratch 23 or the foreign object 24, the edge 403 is included in the light flux d. Furthermore, the scattered light emitted from the wafer edge 403 distributes on the vertical plane in the normal line direction of the edge as shown in FIG. 36. As the result, as shown in FIG. 37, the scattered light 404 emitted from the edge 403 of the wafer 10 distributes in the edge normal line direction with strong directionality in the down view from the place above the wafer 10. The scattered light 405 emitted from the defect 402 does not exhibit remarkable directionality. Therefore, as shown in FIG. 38, one or two detection optical systems located in the edge tangential direction, namely the B detection optical system and B' detection optical system in FIG. 38, are used to detect the scattered light 405 emitted from the defect 402 with stronger intensity than that of the scattered light 404 emitted from the edge 403. Otherwise, one or a plurality of detection optical systems selected from C detection optical system, C' detection optical system, D detection optical system, and D' detection optical system may be used as the detection optical system. Furthermore, the comparison computing unit 18 in the computation processing unit 8 calculates the detected luminance ratio between A detection optical system, A' detection optical system, and above-mentioned detection optical systems to thereby determine the magnitude of the directionality. Thereby, whether there is the defect including only the edge 403 or the defect including the defect 402 is determined.

Figure 24:
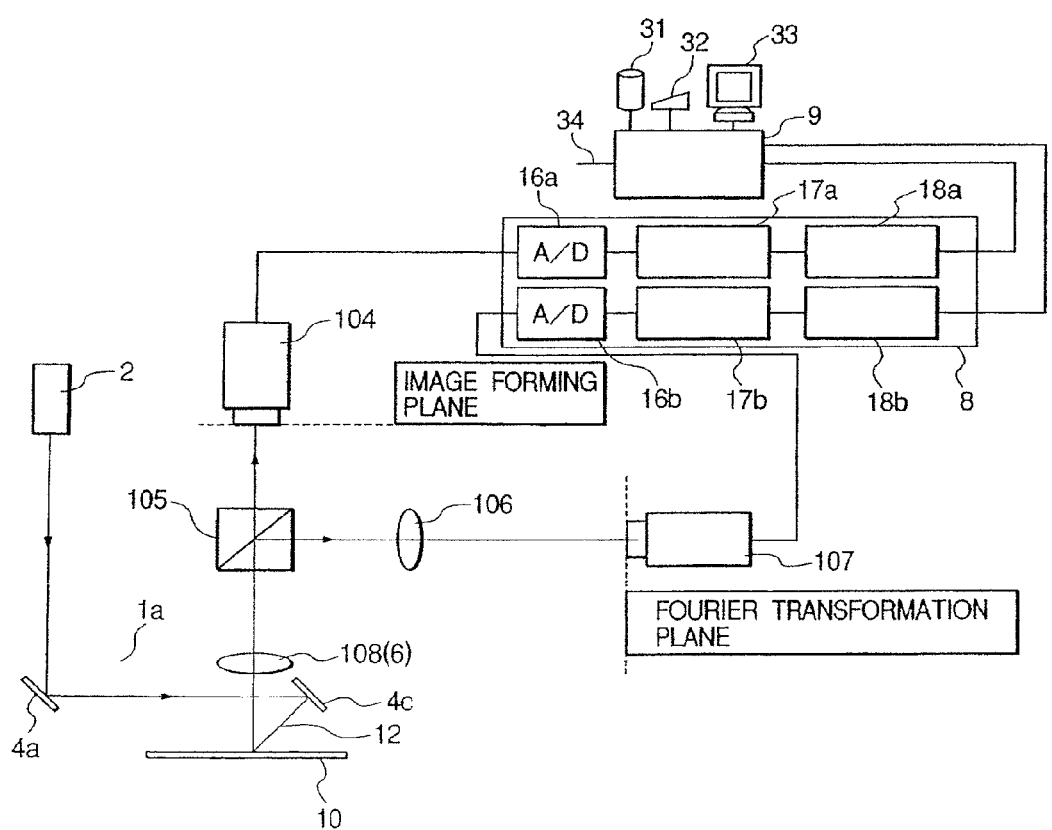
FIG. 24 is a schematic structural diagram illustrating the third example of a surface inspection apparatus in accordance with the present invention.
Figure 39:
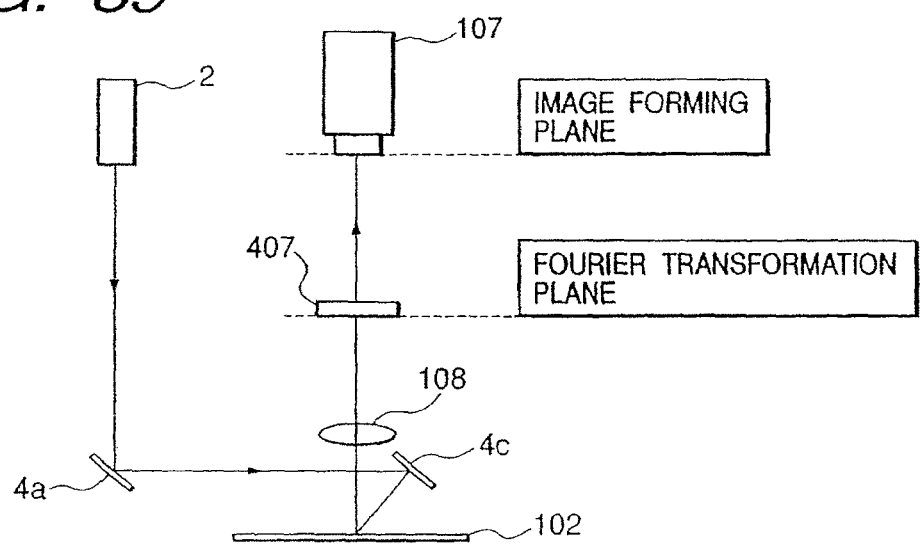
FIG. 39 is an explanatory diagram illustrating another example for discrimination processing between a wafer edge portion and defect.
Figure 40:
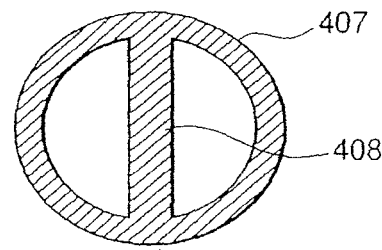
FIG. 40 is a diagram illustrating an example of a space filter used in FIG. 39.

Next, the case in which the present embodiment is applied to the image forming detection optical system shown in FIG. 24 will be described with reference to FIG. 39. In this case, a space filter 407 shown in FIG. 40 is located on the Fourier transformation plane and a space filter shading unit 408 is located in the wafer edge normal line direction. As shown in FIG. 36, the scattered light emitted from the wafer edge 403 distributes from the wafer edge 403 to the normal line direction with strong directionality. Therefore, the space filter 407 is inserted to thereby shade the scattered light emitted from the edge 403, and it is possible for the photoelectric conversion means 107 to receive the scattered light emitted from the defect 402.

In the present embodiment, the case in which an Rθ stage (stage that is rotatable in the horizontal plane) is used as the stage 15. In this case, the direction of the detection optical system and the wafer edge irradiated with the illumination light such as a laser light is relatively stable and constant including orientation flat. Therefore, it is not necessary to change the position of the detection optical systems 5b and 5c to be used in the converging optical system or the shading direction of the space filter 407 in the image forming optical system.

Only an X-Y stage is used as the stage 15, it is necessary to change the detection optical systems 5b and 5c that are used in matching with the edge direction of the wafer or to reverse the space filter 407.

As described, according to the above examples, the foreign object located near the wafer edge can be detected at high sensitivity, and malfunction of the process in which the foreign object is apt to adhere on the peripheral region of the edge is found immediately. As the result, the high yield production can be achieved.

According to the present invention, when a work target such as insulating film is subject to a polishing process such as CMP or a grinding process in the semiconductor/magnetic head manufacturing processes, the present invention exhibits the effect that the scratch of various configurations and the adhered foreign object that occur on the surface are inspected discriminatingly. The present invention makes it possible for the configuration of the scratch to be classified in detail and the cause of the malfunction found promptly. The present invention makes it possible for malfunction of the polishing apparatus to be found promptly because the total inspection or high frequency sampling inspection can be carried out and a prompt and suitable countermeasure applied, making it possible to improve the yield remarkably. The invention may be embodied in other specific forms without departing from the sprit or essential characteristics thereof. The present embodiment is therefore to be considered in all respects as illustrative and not restrictive, and all changes which come within the meaning and range of equivalency of the appended claims are therefore intended to be embraced therein.

What is claimed is:

1. A surface inspection apparatus, comprising:
   a stage configured to support an inspection target mounted thereupon:
   a first illumination optical system configured to illuminate from a first angle the inspection target mounted on the stage;
   a second illumination optical system configured to illuminate from a second angle having a lower elevation angle than the first angle, the inspection target mounted on the stage;
   a reflection light detection system configured to detect a first reflected light reflected from the inspection target after being illuminated by the first illumination optical system, to convert the first reflected light to a first luminance data, to detect a second reflected light reflected from the inspection target after being illuminated by the second illumination optical system, and to convert the second reflected light to a second luminance data;
   a defect classification system configured to recognize first luminance data and second luminance data arising from positions located in close proximity to each other as data of a concatenated defect, and to classify a linear concatenated defect as a scratch by referring to the logical sum of said first luminance data and said second luminance data; and
   an output portion configured to output information of the type of the detect classified in the effect classification system.

2. The surface inspection apparatus according to claim 1, wherein said defect classification system is configured to perform recognition by referring to the logical sum of said first luminance data and said second luminance data.

3. The surface inspection apparatus according to claim 1, wherein said defect classification system is configured to recognize first luminance data arising from positions located in close proximity as data of a concatenated defect, and to classify a linear concatenated defect recognized thereby as a scratch; and
   wherein said defect classification system is configured to recognize second luminance data arising from positions located in close proximity as data of a concatenated defect and to classify a linear concatenated defect recognized thereby as a scratch.

4. The surface inspection apparatus according to claim 3, wherein said defect classification system is configured to remove the data classified as a scratch, and to classify data of the scratch and data of a foreign object by non-removal date.

5. The defect inspection apparatus, as described in claim 1, wherein said reflection light detection system comprises:
   a first detection system configured to detect reflection light reflected from the second angle; and
   a second detection system configured to detect reflection light reflected from a third angle having a lower elevation angle than the second angle; and
   wherein said defect classification system is configured to classify a type of defect by using non-removal data detected by the first and second detection system.

6. The defect inspection apparatus, as described in claim 1, wherein, at least, one of said plurality of first detectors is set to adjust sensitivity.

7. The defect inspection apparatus, as described in claim 1, wherein, at least, one of said plurality of second detectors is set to adjust sensitivity.

8. The defect inspection apparatus, as described in claim 1, wherein the defect inspection apparatus includes an optical path switching mechanism, which switches the illumination by said first illumination optical system and the illumination by said second illumination optical system.

9. The defect inspection apparatus, as described in claim 1, wherein a light source for said first illumination optical system is identical to a light source for said second illumination optical system.

10. The defect inspection apparatus, as described in claim 1, wherein said plurality of first detectors are photomultipliers.

11. The defect inspection apparatus, as described in claim 1, wherein said signal processing system inspects a defect by using the sum of signals detected from said plurality of first detectors.

* * * * *